(12) United States Patent
Kim et al.

(10) Patent No.: US 12,295,938 B2
(45) Date of Patent: May 13, 2025

(54) COMPOSITION FOR TREATING CASTRATION-RESISTANT PROSTATE CANCER, COMPRISING QUASSINOIDS

(71) Applicants: SAMSUNG LIFE PUBLIC WELFARE FOUNDATION, Seoul (KR); RESEARCH & BUSINESS FOUNDATION SUNGKYUNKWAN UNIVERSITY, Gyeonggi-do (KR)

(72) Inventors: Jeong Hoon Kim, Seoul (KR); Byong Chang Jeong, Seoul (KR); Sue Jin Moon, Seoul (KR)

(73) Assignees: SAMSUNG LIFE PUBLIC WELFARE FOUNDATION, Seoul (KR); RESEARCH & BUSINESS FOUNDATION SUNGKYUNKWAN UNIVERSITY, Gyeonggi-do (KR)

( * ) Notice: Subject to any disclaimer, the term of this patent is extended or adjusted under 35 U.S.C. 154(b) by 818 days.

(21) Appl. No.: 17/606,582

(22) PCT Filed: May 22, 2020

(86) PCT No.: PCT/KR2020/006670
§ 371 (c)(1),
(2) Date: Oct. 26, 2021

(87) PCT Pub. No.: WO2020/246737
PCT Pub. Date: Dec. 10, 2020

(65) Prior Publication Data
US 2022/0218660 A1    Jul. 14, 2022

(30) Foreign Application Priority Data

Jun. 4, 2019  (KR) .......................... 10-2019-0066278
May 14, 2020  (KR) .......................... 10-2020-0057894

(51) Int. Cl.
*A61K 31/37* (2006.01)
*A61P 35/00* (2006.01)

(52) U.S. Cl.
CPC .............. *A61K 31/37* (2013.01); *A61P 35/00* (2018.01)

(58) Field of Classification Search
CPC ................................. A61K 31/37; A61P 35/00
See application file for complete search history.

(56) References Cited

FOREIGN PATENT DOCUMENTS

| KR | 10-2009-0113852 A | 11/2009 |
| KR | 10-2017-0012562 A | 2/2017 |
| KR | 10-2018-0040138 A | 4/2018 |
| KR | 10-1884960 B1 | 8/2018 |

OTHER PUBLICATIONS

Lichota, A. et al ( Int. J. Mol. Sci. 2018, 19, 3533; doi: 10.3390/ijms19113533).
International Search Report from corresponding PCT Application No. PCT/KR2020/006670, dated Sep. 10, 2020.

*Primary Examiner* — Kamal A Saeed
(74) *Attorney, Agent, or Firm* — Harness, Dickey & Pierce, P.L.C.

(57) ABSTRACT

The present invention relates to: a composition for treating castration-resistant prostate cancer, comprising quassinoids; and a method for treating castration-resistant prostate cancer by using same.

4 Claims, 30 Drawing Sheets

| Structure | Name |
|---|---|
| 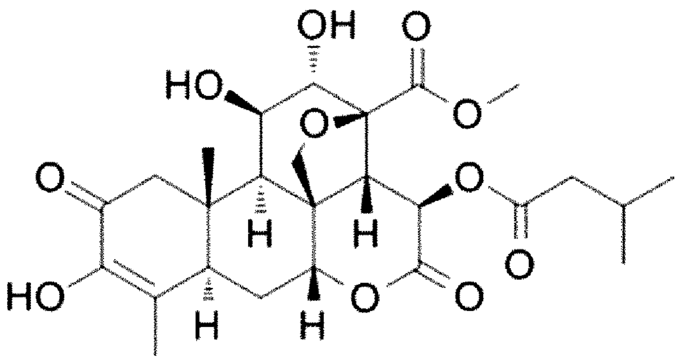 | Bruceine A |
| 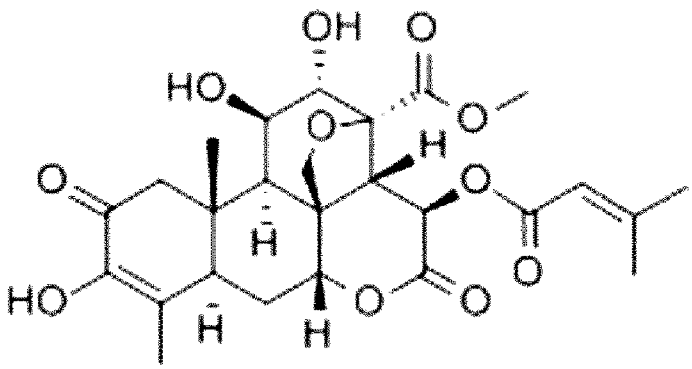 | Brusatol |
| 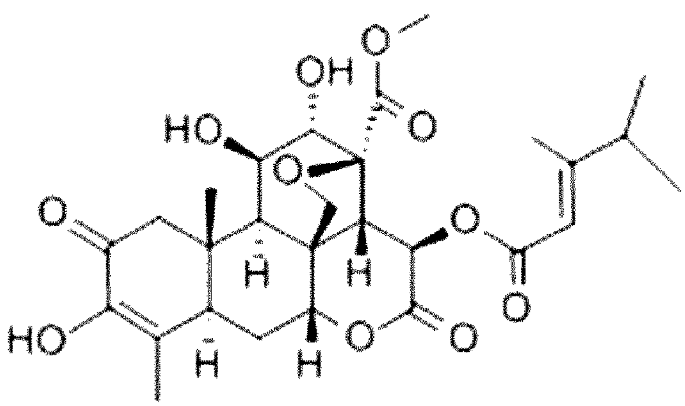 | Bruceantin |

COMPOSITION FOR TREATING CASTRATION-RESISTANT PROSTATE CANCER, COMPRISING QUASSINOIDS

CROSS-REFERENCE TO RELATED APPLICATIONS

This application is a national phase application of PCT Application No. PCT/KR2020/006670, filed on May 22, 2020, which claims priority to Korean Patent Application Nos. 10-2019-0066278, filed on Jun. 4, 2019 and 10-2020-0057894, filed on May 14, 2020. The entire disclosures of the applications identified in this paragraph are incorporated herein by references.

TECHNICAL FIELD

The present disclosure relates to a composition comprising a quassinoid for treatment of castration-resistant prostate cancer and a method for treatment of castration-resistant prostate cancer, using same.

BACKGROUND ART

Prostate cancer is the most common cancer in men, ranking second in the cancer mortality rate for men in the United States, and the importance of diagnosis and treatment of prostate cancer is emerging as the incidence thereof increases by 10.5% every year in Korea.

The androgen receptor (hereinafter referred to as "AR") is a transcription factor that plays a pivotal role in the onset and progression of prostate cancer, with 90% or greater of cases accounted for by AR-positive prostate cancer.

AR is a ligand-dependent transcription factor that is activated as it binds to the ligand androgen. Prostate specific antigen (PSA), which is a representative target of AR, is utilized as a representative diagnosis marker.

Typically used in treating prostate cancer is androgen deprivation therapy (hereinafter referred to as "ADT") in which the synthesis of androgen is inhibited to indirectly suppress the transcriptional activity of AR or anti-androgen therapy in which a medicine binds directly to AR to inhibit the transcriptional activity of AR.

Prostate cancer, although initially responding to both of the therapies, eventually progresses to castration-resistant prostate cancer (hereinafter referred to as "CRPC"). However, there are actually no therapies for CRPC.

Various causes including AR and coactivator gene amplification, mutations, etc. are known to be responsible for the mechanisms of CRPC progression. In recent years, the expression of AR-V7, which is an AR variant resulting from splicing of the C-terminal binding domain in AR protein, has been reported to be a leading cause of progression into CRPC.

Lacking the ligand-binding domain, AR-V7 exhibits ligand-independent transcriptional activity and acts as a main factor promotive of the progression of CRPC because it is resistant to pre-existing medications developed to targeting the C-terminal domain of AR.

There is therefore a need for developing a new therapy targeting both AR and AR-V7 in order to overcome limitations of such conventional therapies.

SUMMARY

Technical Problem

Recent reports have reported that drugs such as ailanthone and artesunate repress both transcriptional activity of AR and AR-V7 to inhibit in vitro and in vivo growth of CRPC cells, raising the possibility that drugs can be used as therapeutic agents for CRPC.

Based on the fact the reported drugs are all natural products and have antimalarial activity, the present inventors have constructed a library of about 40 natural products reported to be of anti-malarial activity and screened the library to explore the possibility of repositioning antimalarials as drugs capable of inhibiting transcriptional activity of both AR/AR-V7.

Accordingly, an aspect of the present disclosure is to provide a pharmaceutical composition comprising a quassinoid for treatment of castration-resistant prostate cancer.

Another aspect of the present disclosure is to provide a method for treatment of castration-resistant prostate cancer, the method comprising a step of administering a therapeutically effective amount of quassinoid to a subject in need thereof.

Another aspect of the present disclosure is to a use of a quassinoid for treating castration-resistant prostate cancer.

Solution to Problem

The present disclosure relates to a composition comprising a quassinoid for treatment of castration-resistant prostate cancer and a method for treatment of castration-resistant prostate cancer.

Below, a detailed description will be given of the present disclosure.

An aspect of the present disclosure is concerned with a pharmaceutical composition comprising a quassinoid for treatment of castration-resistant prostate cancer.

As used herein, the term "castration-resistant prostate cancer" (CRPC) refers to prostate cancer that continues to grow even when the blood testosterone levels are at or below the castrate level. Prostate cancer in an early stage requires androgen hormone for the growth thereof whereas the growth of castration-resistant prostate cancer, which is resistant to androgen blockade (deprivation) therapy, continues even in the absence of androgen hormone. Patients with such cancer exhibit very poor prognosis as the cancer progresses even after the testosterone levels are reduced to the castrate level by radiotherapy, surgical therapy, chemotherapy, or the like.

In the present disclosure, the quassinoid may be at least one selected from the group consisting of bruceine A, brusatol, and bruceantin, and may be, for example, bruceantin.

In the present disclosure, the bruceine A may be the compound having chemical formula 1, below.

[Chemical Formula 1]

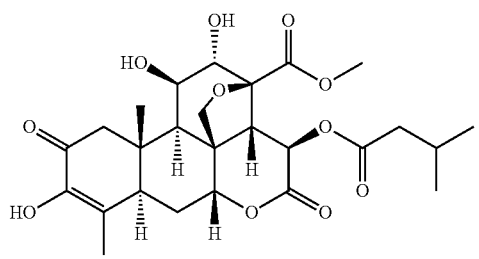

In the present disclosure, the brusatol may be the compound having chemical formula 2, below.

[Chemical Formula 2]

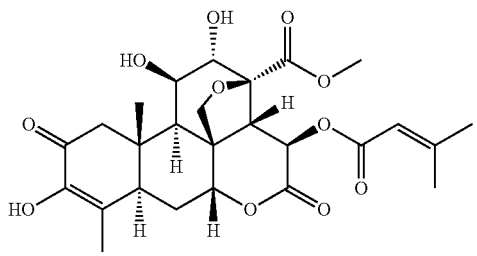

In the present disclosure, the bruceantin may be the compound having chemical formula 3, below.

[Chemical Formula 3]

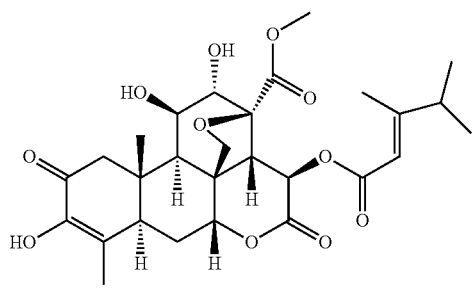

The pharmaceutical composition according to the present disclosure may be administered via various routes.

All administration modes including oral, dermal, venous, muscular, subcutaneous routes, and the like may be contemplated in the present disclosure. For example, administration may take a subcutaneous or oral route, but with no limitations thereto.

The pharmaceutical composition of the present disclosure may be formulated into oral dosage forms such as pulvises, granules, tablets, capsules, ointments, suspensions, emulsions, syrups, aerosols, etc., or parenteral dosage forms such as transdermal agents, suppositories, and sterile injectable solutions according to typical methods.

The pharmaceutical composition of the present disclosure may further comprise a pharmaceutically suitable and physiologically acceptable auxiliary agent such as a carrier, an excipient, and a diluent.

Examples of carriers, excipients, and diluents that may be contained in the pharmaceutical composition of the present disclosure include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

In formulating the pharmaceutical composition of the present disclosure, a diluent or an excipient such as a filler, a thickener, a binder, a humectant, a disintegrant, a surfactant, etc. may be used.

Solid formulations for oral administration of the pharmaceutical composition of the present disclosure may take the forms of tablets, pills, pelvises, granules, capsules, and the like. Such solid formulations may be prepared by blending the extract with at least one excipient, for example, starch, calcium carbonate, sucrose, or lactose, gelatin, etc.

In addition to simple excipients, lubricants such as magnesium stearate, talc, etc. may be employed. Formulations for oral administration, exemplified by suspension, solutions for internal use, emulsions, syrups, ointments, etc., may include various excipients, for example, humectants, sweeteners, aromatics, preservatives, etc., in addition to simple diluents, such as water, liquid paraffin, etc.

Examples of formulations for parenteral administration of the pharmaceutical composition of the present disclosure include sterile aqueous solutions, non-aqueous solutions, suspensions, emulsions, lyophilizates, suppositories, transdermal agents, etc. As the non-aqueous solutions and suspending agents, propylene glycol, polyethylene glycol, vegetable oil such as olive oil, injectable ester such as ethyl oleate, and the like may be used. As a base for suppositories, Witepsol, Macrogol, Tween 61, cacao butter, laurin butter, glycerogelatin, and the like may be used.

According to embodiments of applying the pharmaceutical composition of the present disclosure to human bodies, the pharmaceutical composition of the present disclosure may be administered alone to human bodies. However, taking into account the conventional manner of administration and the standard pharmaceutical practice, it may be administered after being mixed with the selected pharmaceutical carriers.

The pharmaceutical composition of the present disclosure may be orally, buccally or sublingually administered in the form of a tablet containing starch or lactose, in the form of a capsule of the composition alone or containing some excipients, or in the form of an elixir or suspension containing some chemicals which provide taste or color.

Such liquid preparations may be formulated together with the pharmaceutically acceptable additives such as a suspending agent (e.g., glycerides mixtures such as semi-synthetic glycerides including methyl cellulose or witepsol, or apricot kernel oil with PEG-6 ester, or PEG-8 with caprylic/capric glyceride).

A suitable dose of the pharmaceutical composition of the present disclosure varies depending on the patient's age, body weight, and sex, the mode of administration, health conditions, and disease severity and may be administered once or several times a day with regular time intervals according to the decisions of physicians or pharmacists. The pharmaceutical composition of the present disclosure may be administered at a dose of 1 mg/kg or higher every 2 days or at a dose of 2 mg/kg or higher every 2 days, for example, 2 mg/kg every 2 days, with no limitations thereto.

Advantageous Effects of Invention

The present disclosure relates to a composition comprising a quassinoid for treatment of castration-resistant prostate cancer and a method for treatment of castration-resistant prostate cancer, using the same. Whereas conventional hormone therapies have the limitation of being unable to target both AR and AR-V7, the present disclosure can target both AR and AR-V7 and exhibits 10- to 20-fold higher potent pharmaceutical efficacy than ailanthone, which has been being developed into a therapeutic agent for castration-resistant prostate cancer.

BEST MODE FOR CARRYING OUT THE INVENTION

A pharmaceutical composition comprising a quassinoid for treatment of castration-resistant prostate cancer.

DETAILED DESCRIPTION

A better understanding of the present disclosure may be obtained via the following examples which are set forth to illustrate, but are not to be construed as limiting the present disclosure.

Example 1. Screening

A library of antimalarial agents was screened using a luciferase reporter assay to measure changes in AR/AR-V7 transcriptional activity.

Figure 1A:
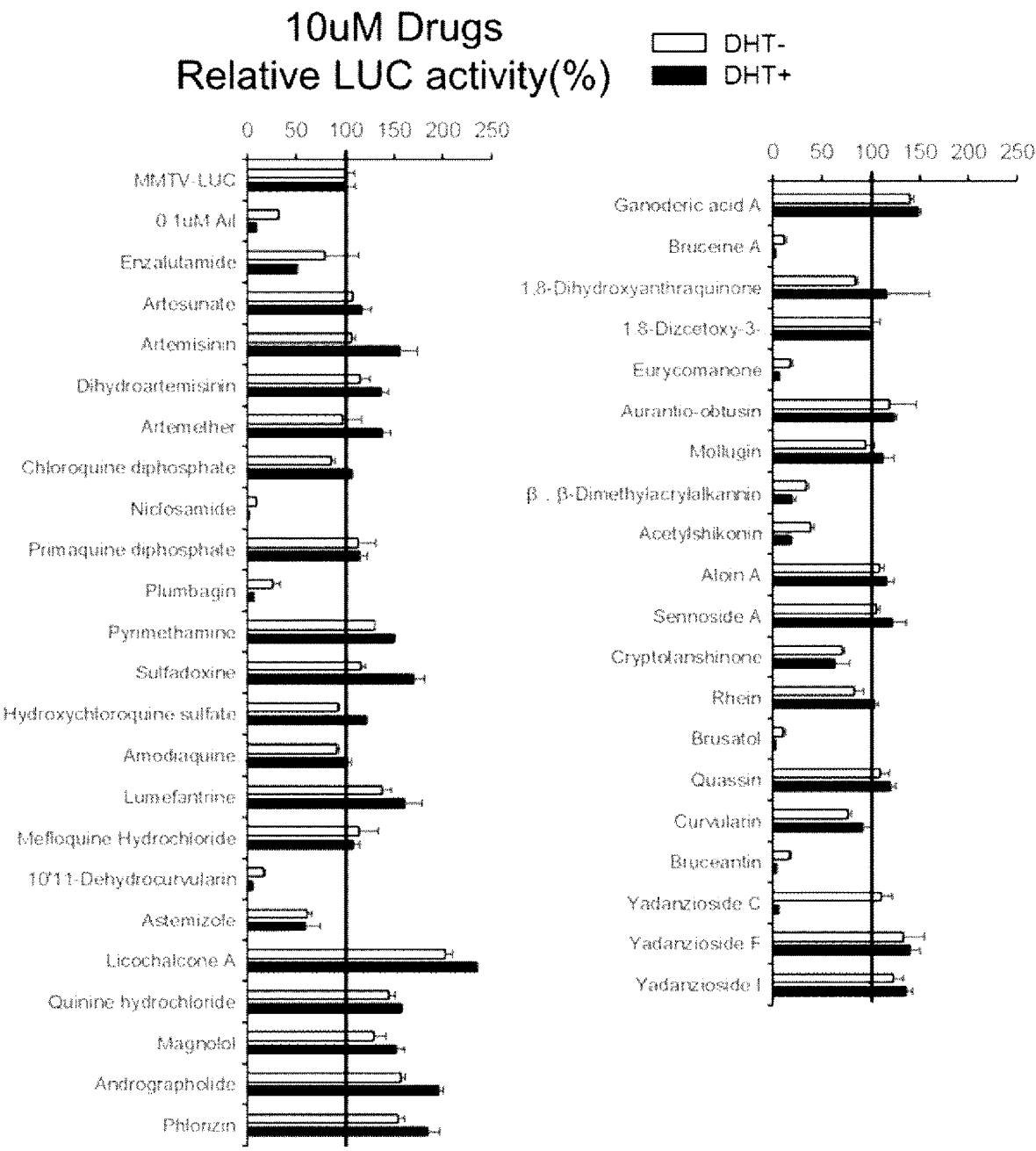
FIG. 1a shows graphs of primary inhibitor candidates against AR/AR-V7 transcriptional activity, explored through screening of a library of antimalarial agents using a reporter gene assay based on the castration-resistant prostate cell line 22RV1 according to an embodiment of the present disclosure.
Figure 1B:
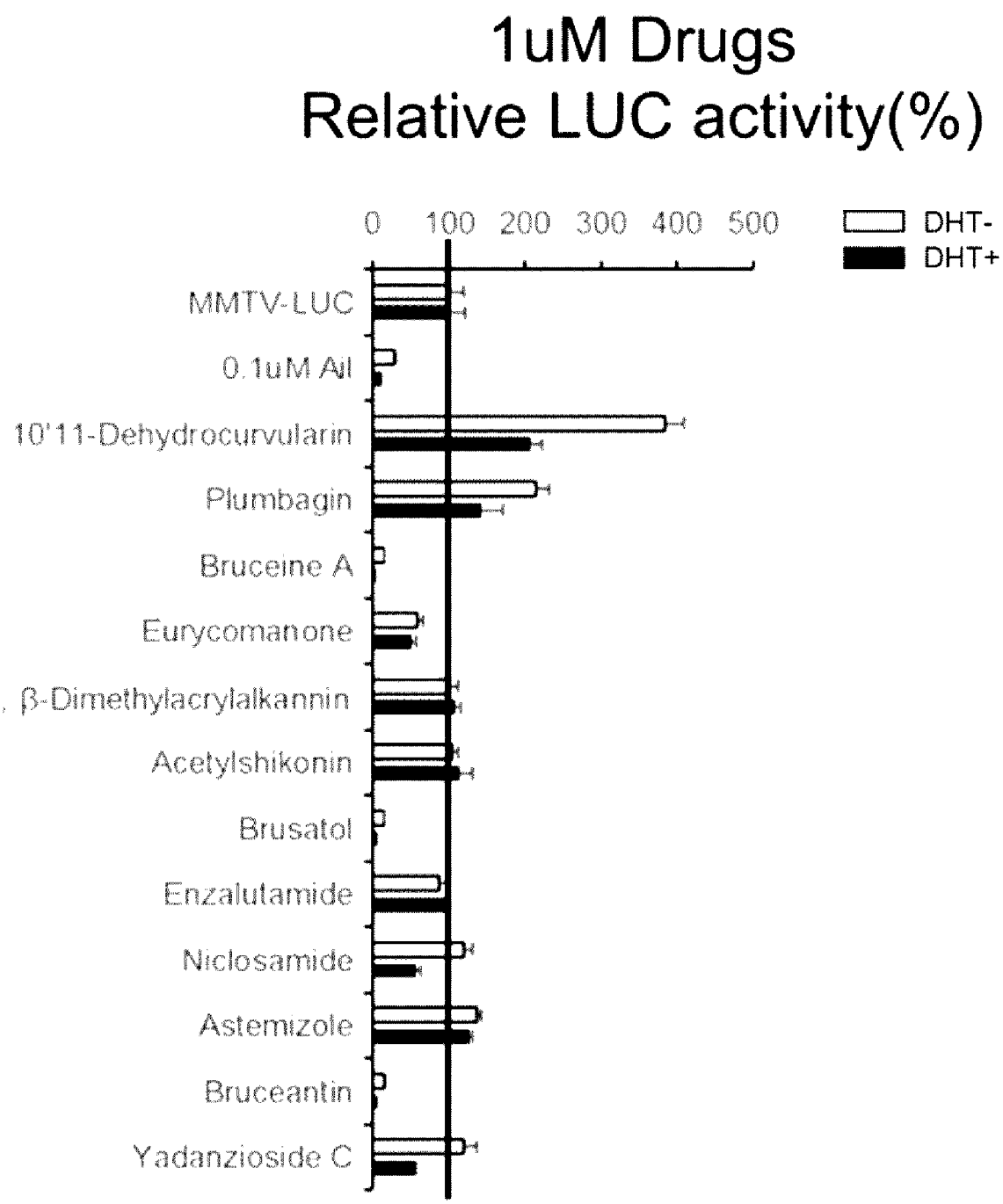
FIG. 1b is a graph of secondary inhibitor candidates against AR/AR-V7 transcriptional activity, explored through screening of a library of antimalarial agents according to an embodiment of the present disclosure.
Figure 1C:
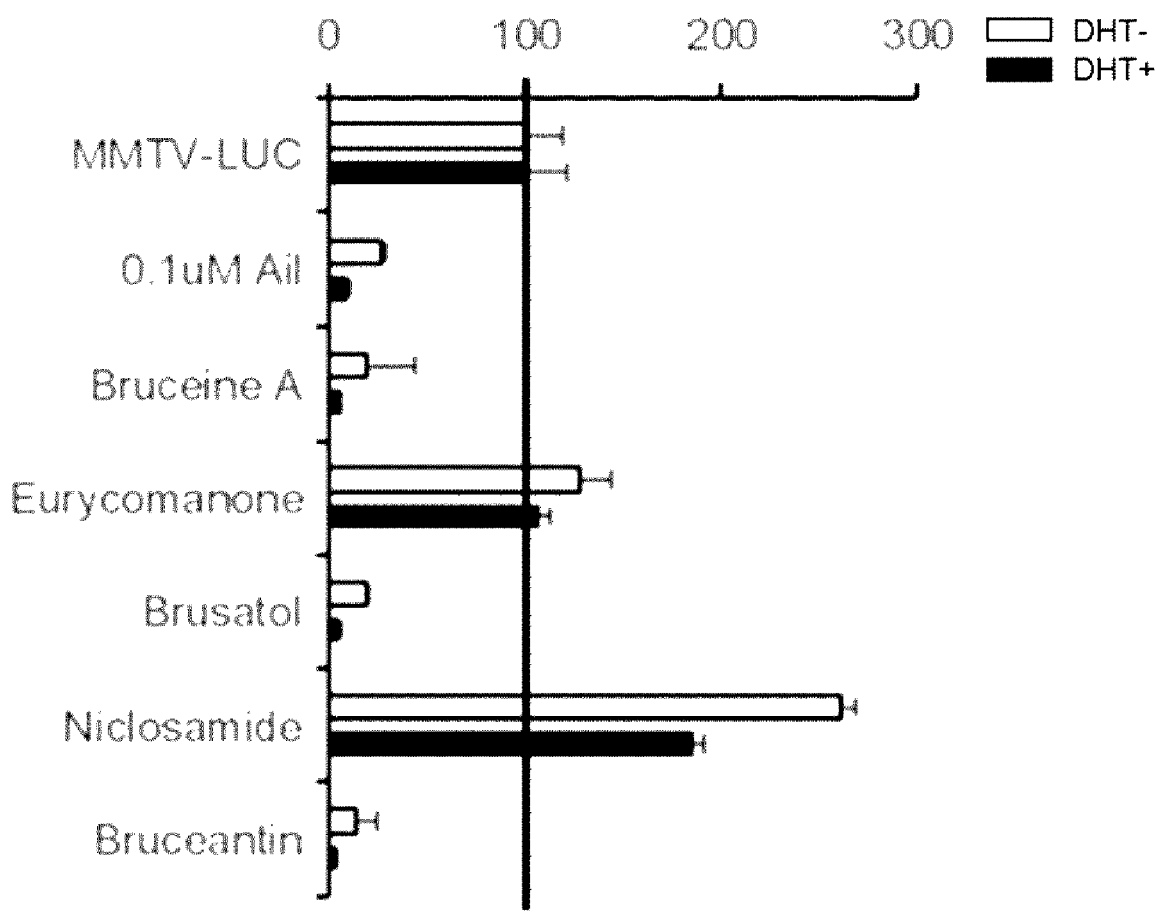
FIG. 1c is a graph of tertiary inhibitor candidates against AR/AR-V7 transcriptional activity, explored through screening of a library of antimalarial agents according to an embodiment of the present disclosure.

Briefly, 22RV1 cells, which are representative CRPC cells expressing transcriptional activity of both AR and AR-V7, were transfected with a MMTV-LUC reporter capable of measuring both AR and AR-V7 and treated with various drugs according to the presence and absence of the androgen hormone dihydrotestosterone (hereinafter referred to as "DHT") (DHT+, conditions for measuring AR transcriptional activity; DHT−, condition for measuring AR-V7 transcriptional activity), followed by measuring changes in AR and AR-V7 transcriptional activity. Screening was made primarily with 10 μM of each drug. Drugs with 50% or higher inhibition against the transcriptional activity were selected and then each used at a concentration of 1 μM for secondary screening and at a concentration of 0.1 μM for tertiary screening. The results are depicted in FIGS. 1a to 1c and summarized in Tables 1 to 3.

TABLE 1

| Conc. | Compound | MMTV-LUC activity (%) DHT− | MMTV-LUC activity (%) DHT+ |
|---|---|---|---|
| | — | 100.0 ± 9.2 | 100.0 ± 8.7 |
| 10 uM | Enzalutamide | 79.4 ± 34.6 | 51.8 ± 0.1 |
| | Ailnahtone | 11.6 ± 3.2 | 2.5 ± 0.4 |
| | Artesunate | 107.6 ± 0.8 | 117.5 ± 9.3 |
| | Artemisinin | 106.7 ± 4.3 | 156.1 ± 17.6 |
| | Dihydroartemisinin | 115.3 ± 10.1 | 137.5 ± 7.0 |
| | Artemether | 97.5 ± 19.5 | 138.2 ± 8.8 |
| | Chloroquine diphosphate | 86.3 ± 3.5 | 106.9 ± 1.0 |
| | Niclosamide | 9.4 ± 0.6 | 2.3 ± 0.5 |
| | Primaquine diphosphate | 113.8 ± 17.6 | 115.6 ± 7.0 |
| | Plumbagin | 26.0 ± 7.6 | 7.1 ± 0.1 |
| | Pyrimethamine | 130.5 ± 0.2 | 149.2 ± 2.4 |
| | Sulfadoxine | 116.5 ± 4.4 | 170.3 ± 11.2 |
| | Hydroxychloroquinesulfate | 92.3 ± 2.0 | 122.1 ± 0.7 |
| | Amodiaquine dihydrochloride dihydrate | 91.6 ± 2.9 | 102.2 ± 4.3 |
| | Lumefantrine | 137.7 ± 9.5 | 160.7 ± 18.2 |
| | MefloquineHydrochloride | 114.3 ± 20.3 | 109.0 ± 6.3 |
| | 10,11-Dehydrocurvularin | 16.3 ± 2.5 | 5.5 ± 0.6 |
| | Astemizole | 61.2 ± 5.0 | 59.5 ± 15.5 |
| | Licochalcone A | 202.7 ± 7.1 | 235.6 ± 0.2 |
| | Quinine hydrochloride | 145.1 ± 6.6 | 156.9 ± 2.3 |
| | Magnolol | 129.6 ± 12.0 | 151.9 ± 8.6 |
| | Andrographolide | 157.3 ± 4.3 | 196.2 ± 5.0 |
| | Phlorizin | 154.5 ± 6.6 | 184.4 ± 12.6 |
| | Ganoderic acid A | 140.0 ± 3.8 | 148.9 ± 2.8 |
| | Bruceine A | 11.0 ± 2.5 | 2.8 ± 0.2 |
| | 1,8-Dihydroxyanthraquinone | 83.8 ± 2.9 | 116.0 ± 43.8 |
| | 1,8-Diacetoxy-3-carboxyanthraquinone | 101.0 ± 8.7 | 98.5 ± 2.1 |
| | Eurycomanone | 17.7 ± 2.7 | 6.7 ± 0.5 |
| | Aurantio-obtusin | 119.2 ± 27.4 | 124.3 ± 2.2 |

TABLE 1-continued

| Conc. | Compound | MMTV-LUC activity (%) DHT− | MMTV-LUC activity (%) DHT+ |
|---|---|---|---|
| | Mollugin | 94.7 ± 9.5 | 112.4 ± 11.1 |
| | β,β-Dimethylacrylalkannin | 33.3 ± 3.2 | 19.9 ± 3.5 |
| | Acetylshikonin | 38.6 ± 3.2 | 17.7 ± 1.5 |
| | Aloin A | 108.3 ± 5.0 | 116.3 ± 7.2 |
| | Sennoside A | 105.5 ± 4.4 | 122.3 ± 14.2 |
| | Cryptotanshinone | 70.3 ± 3.2 | 62.7 ± 15.3 |
| | Rhein | 83.0 ± 9.2 | 103.6 ± 3.7 |
| | Brusatol | 10.3 ± 2.7 | 3.2 ± 0.2 |
| | Quassin | 109.8 ± 9.0 | 120.4 ± 5.6 |
| | Curvularin | 76.8 ± 3.0 | 91.6 ± 9.4 |
| | Bruceantin | 16.4 ± 2.3 | 3.9 ± 0.4 |
| | Yadanzioside C | 110.4 ± 11.6 | 5.8 ± 0.7 |
| | Yadanzioside F | 133.6 ± 21.7 | 139.5 ± 11.0 |
| | Yadanzioside I | 123.2 ± 10.4 | 136.0 ± 7.1 |
| | Bruceantinol | 81.2 ± 62.1 | 44.5 ± 2.1 |
| | Bruceanic acid C | 68.5 ± 6.3 | 85.8 ± 14.2 |
| | Brucein D | 7.9 ± 1.3 | 1.1 ± 0.1 |
| | Bruceantinoside A | 6.5 ± 0.9 | 3.8 ± 1.1 |
| | Dehydrobruceine A | 133.8 ± 14.5 | 164.2 ± 16.0 |
| | (+)-Glaucarubinone | 107.6 ± 26.5 | 117.7 ± 3.5 |
| | Yadanziolide A | 8.0 ± 0.6 | 4.1 ± 0.2 |
| | Yadanziolide B | 8.2 ± 1.0 | 4.0 ± 0.5 |
| | Yadanziolide C | 6.0 ± 0.7 | 1.1 ± 0.1 |

TABLE 2

| Conc. | Compound | MMTV-LUC activity (%) DHT− | MMTV-LUC activity (%) DHT+ |
|---|---|---|---|
| | — | 100.0 ± 10.1 | 100.0 ± 11.4 |
| 1 uM | Enzalutamide | 87.4 ± 11.3 | 96.7 ± 1.7 |
| | Ailnahtone | 15.5 ± 2.4 | 4.5 ± 0.9 |
| | Niclosamide | 119.0 ± 10.8 | 56.7 ± 5.3 |
| | Plumbagin | 214.8 ± 16.1 | 142.9 ± 27.5 |
| | 10,11-Dehydrocurvularin | 383.1 ± 24.6 | 206.9 ± 15.0 |
| | Astemizole | 136.4 ± 6.4 | 126.4 ± 3.6 |
| | Bruceine A | 13.5 ± 1.7 | 3.6 ± 0.2 |
| | Eurycomanone | 59.1 ± 7.6 | 51.3 ± 4.6 |
| | β,β-Dimethylacrylalkannin | 100.2 ± 11.4 | 107.9 ± 7.0 |
| | Acetylshikonin | 103.0 ± 7.7 | 113.0 ± 16.6 |
| | Brusatol | 14.0 ± 1.3 | 4.0 ± 0.5 |
| | Bruceantin | 15.2 ± 1.6 | 4.4 ± 0.3 |
| | Yadanzioside C | 118.9 ± 18.1 | 55.6 ± 0.7 |
| | Bruceantinol | 73.5 ± 11.9 | 118.9 ± 21.8 |
| | Brucein D | 7.0 ± 1.2 | 2.0 ± 0.2 |
| | Bruceantinoside A | 11.5 ± 5.6 | 8.0 ± 0.2 |
| | Yadanziolide A | 54.1 ± 13.0 | 58.3 ± 10.9 |
| | Yadanziolide B | 7.2 ± 0.8 | 4.2 ± 0.4 |
| | Yadanziolide C | 17.4 ± 3.1 | 12.1 ± 2.0 |

TABLE 3

| Conc. | Compound | MMTV-LUC activity (%) DHT− | MMTV-LUC activity (%) DHT+ |
|---|---|---|---|
| | — | 100.0 ± 8.9 | 100.0 ± 3.0 |
| 0.1 uM | Ailnahtone | 27.0 ± 2.0 | 9.2 ± 0.4 |
| | Bruceine A | 19.5 ± 20.7 | 5.7 ± 1.0 |
| | Eurycomanone | 127.9 ± 12.0 | 107.7 ± 4.7 |
| | Brusatol | 18.9 ± 20.2 | 5.7 ± 0.6 |
| | Bruceantin | 13.4 ± 2.5 | 4.0 ± 0.5 |
| | Brucein D | 46.0 ± 6.4 | 32.6 ± 6.2 |
| | Bruceantinoside A | 44.9 ± 5.5 | 61.0 ± 7.3 |
| | Yadanziolide C | 80.5 ± 2.9 | 92.5 ± 0.9 |
| | Yadanziolide B | 23.1 ± 5.2 | 32.8 ± 9.0 |

Figure 2:
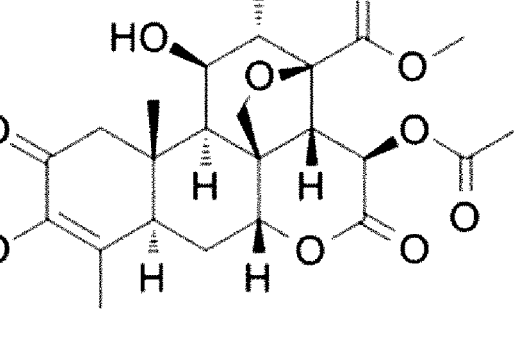
FIG. 2 is a view illustrating chemical structures of quassinoids selected through screening according to an embodiment of the present disclosure.
Figure 2:
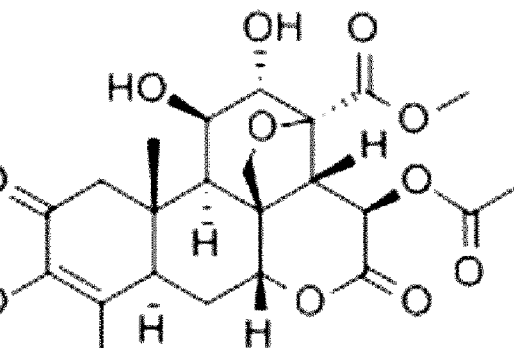
Figure 2:
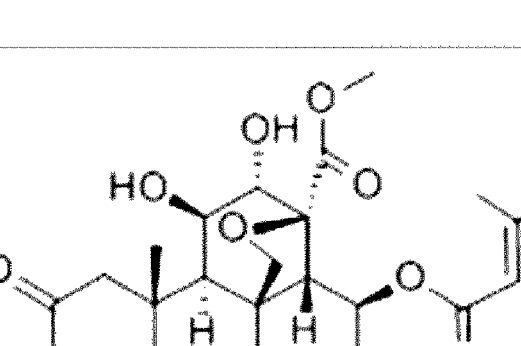

As can be seen in FIGS. 1a to 1c and Tables 1 to 3, the quassinoids bruceantin, brusatol, and bruceine A were explored as potent candidates inhibitory of both AR/AR-V7 transcriptional activity, and their structural formulas are given in FIG. 2.

Example 2. Inhibitory Activity Against AR-V7 and AR Transcriptional Activity and IC$_{50}$ Assay Ailanthone, which was recently reported to be the most potent inhibitor against both AR/AR-V7 transcriptional activity, was used as a reference compound in the assay.

Figure 3A:
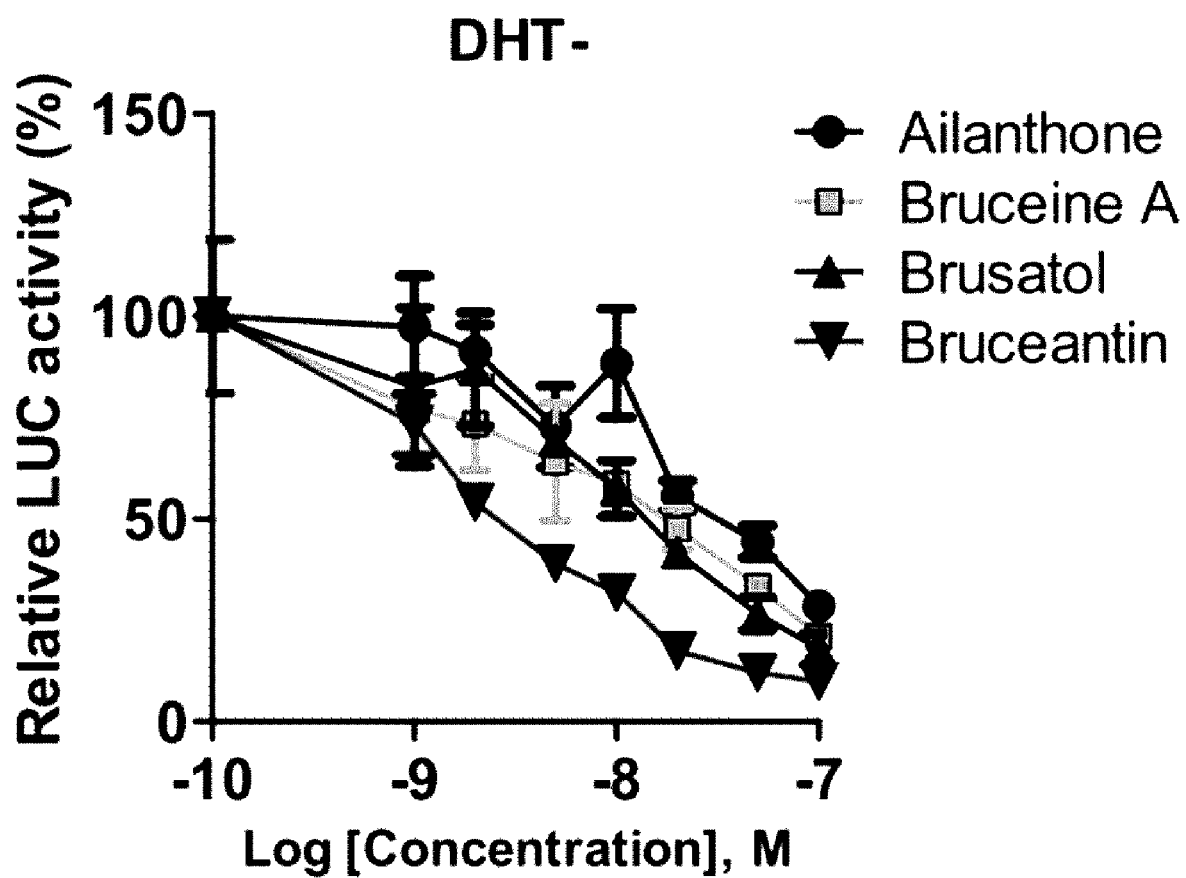
FIG. 3a is a graph showing inhibitory effects of the selected quassinoids and the reference compound ailanthone on transcriptional activity of AV-V7 and AR variants in the CRPC cell line 22RV1, along with analyzed $IC_{50}$ values, according to an embodiment of the present disclosure.
Figure 3B:
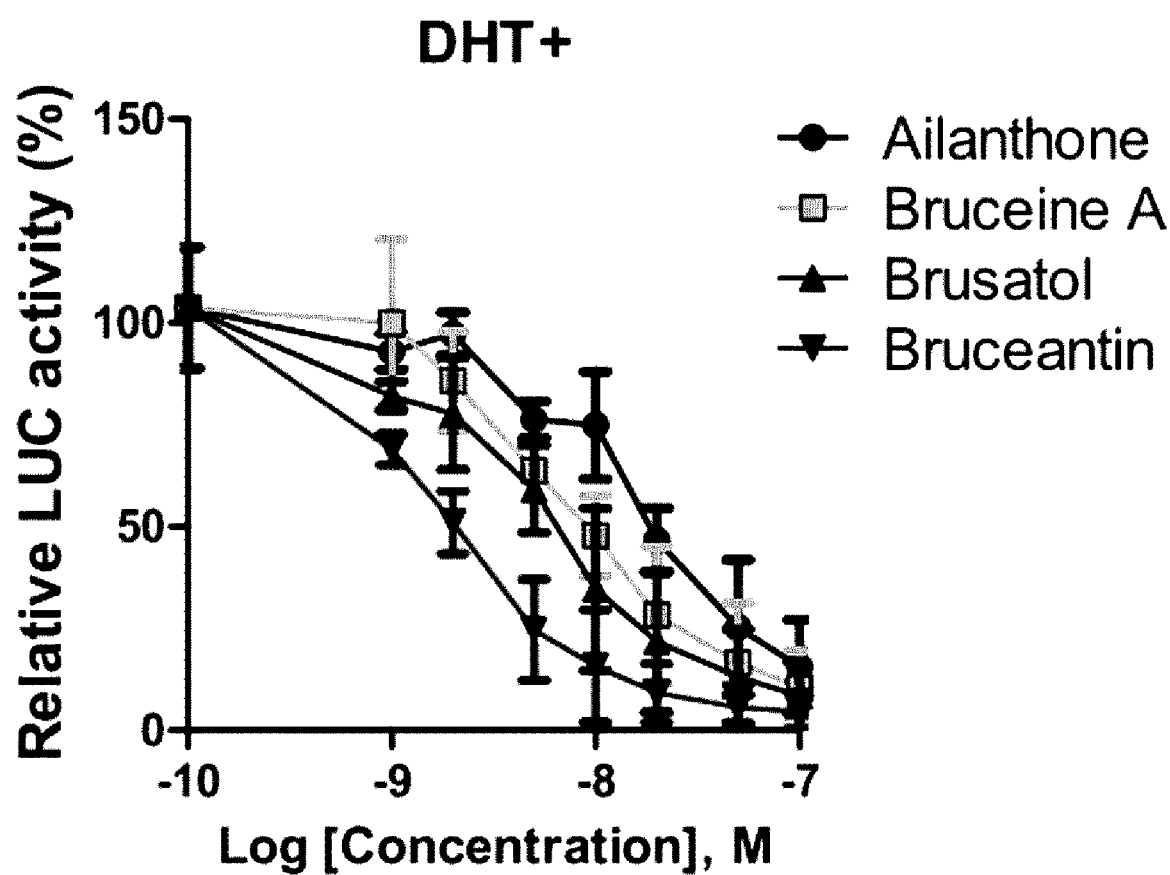
FIG. 3b is a graph showing inhibitory effects of the selected quassinoids and the reference compound ailanthone on androgen-dependent AR transcriptional activity in the CRPC cell line 22RV1, along with analyzed $IC_{50}$ values, according to an embodiment of the present disclosure.
Figure 4A:
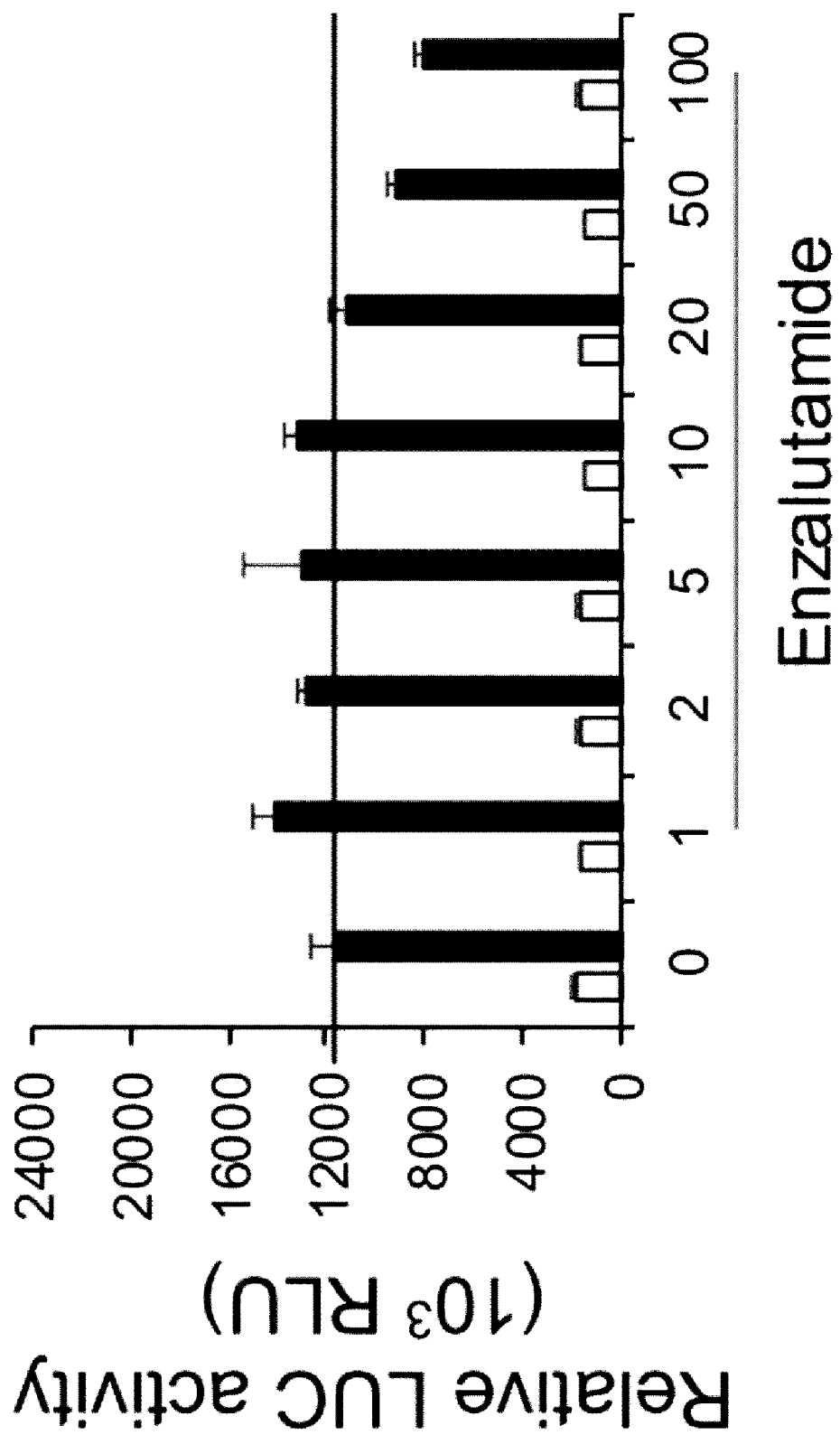
FIG. 4a is a graph showing inhibitory effects of enzalutamide on hormone-dependent AR transcriptional activity of the androgen-dependent prostate cancer cell line LNCaP, along with analyzed $IC_{50}$ values, according to an embodiment of the present disclosure.
Figure 4B:
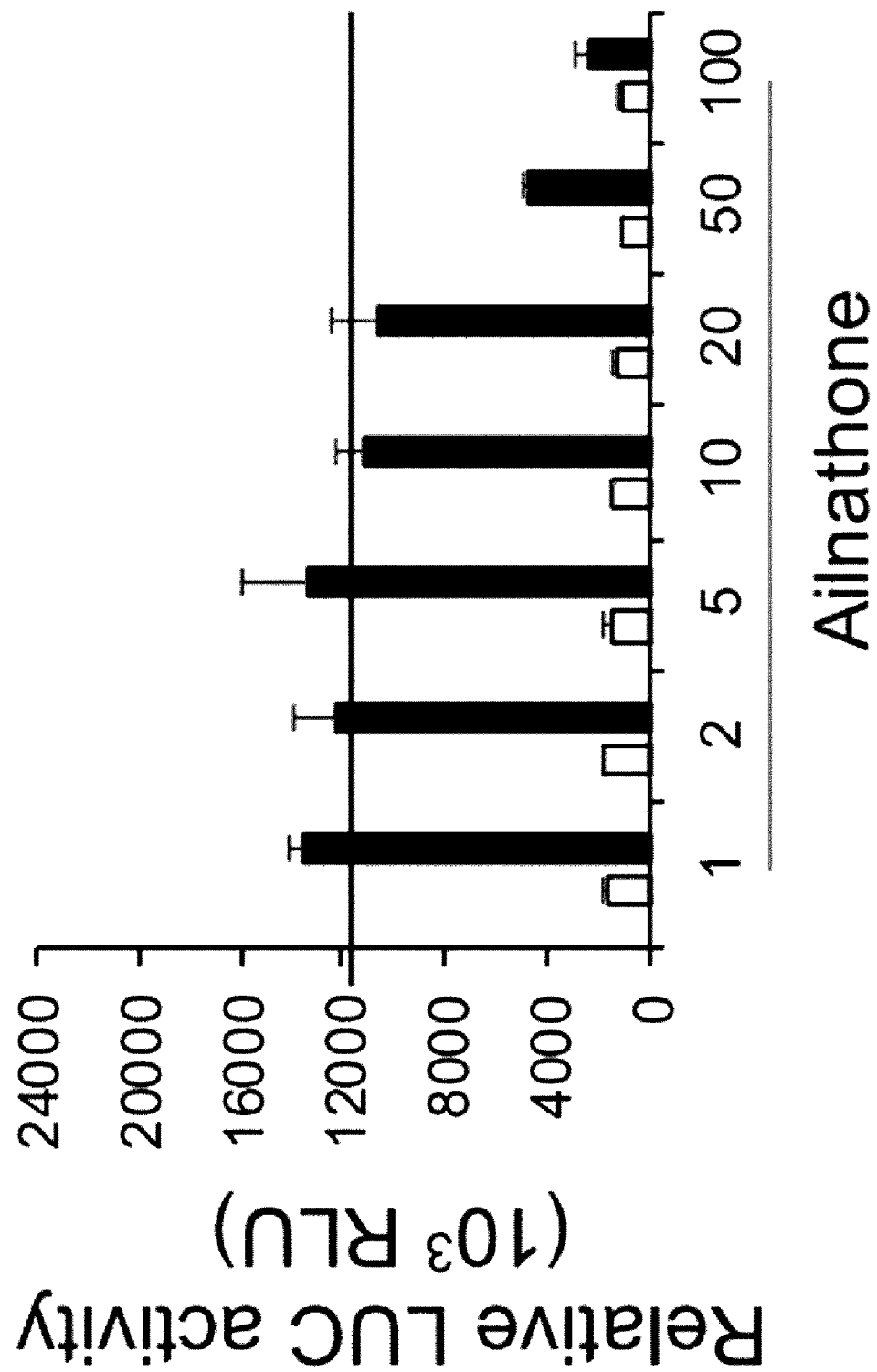
FIG. 4b is a graph showing inhibitory effects of ailanthone on hormone-dependent AR transcriptional activity of the androgen-dependent prostate cancer cell line LNCaP, along with analyzed $IC_{50}$ values, according to an embodiment of the present disclosure.
Figure 4C:
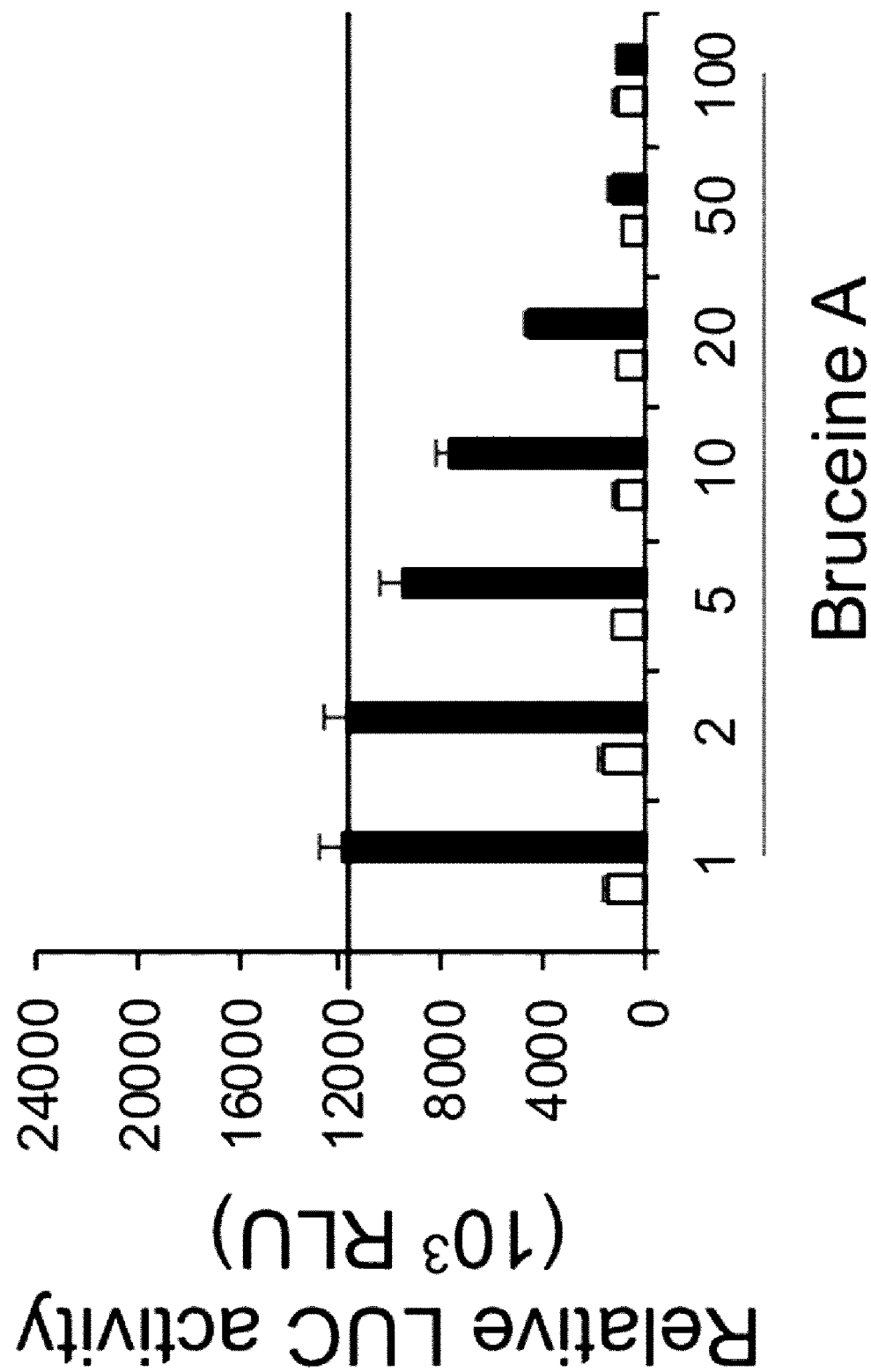
FIG. 4c is a graph showing inhibitory effects of bruceine A on hormone-dependent AR transcriptional activity of the androgen-dependent prostate cancer cell line LNCaP, along with analyzed $IC_{50}$ values, according to an embodiment of the present disclosure.
Figure 4D:
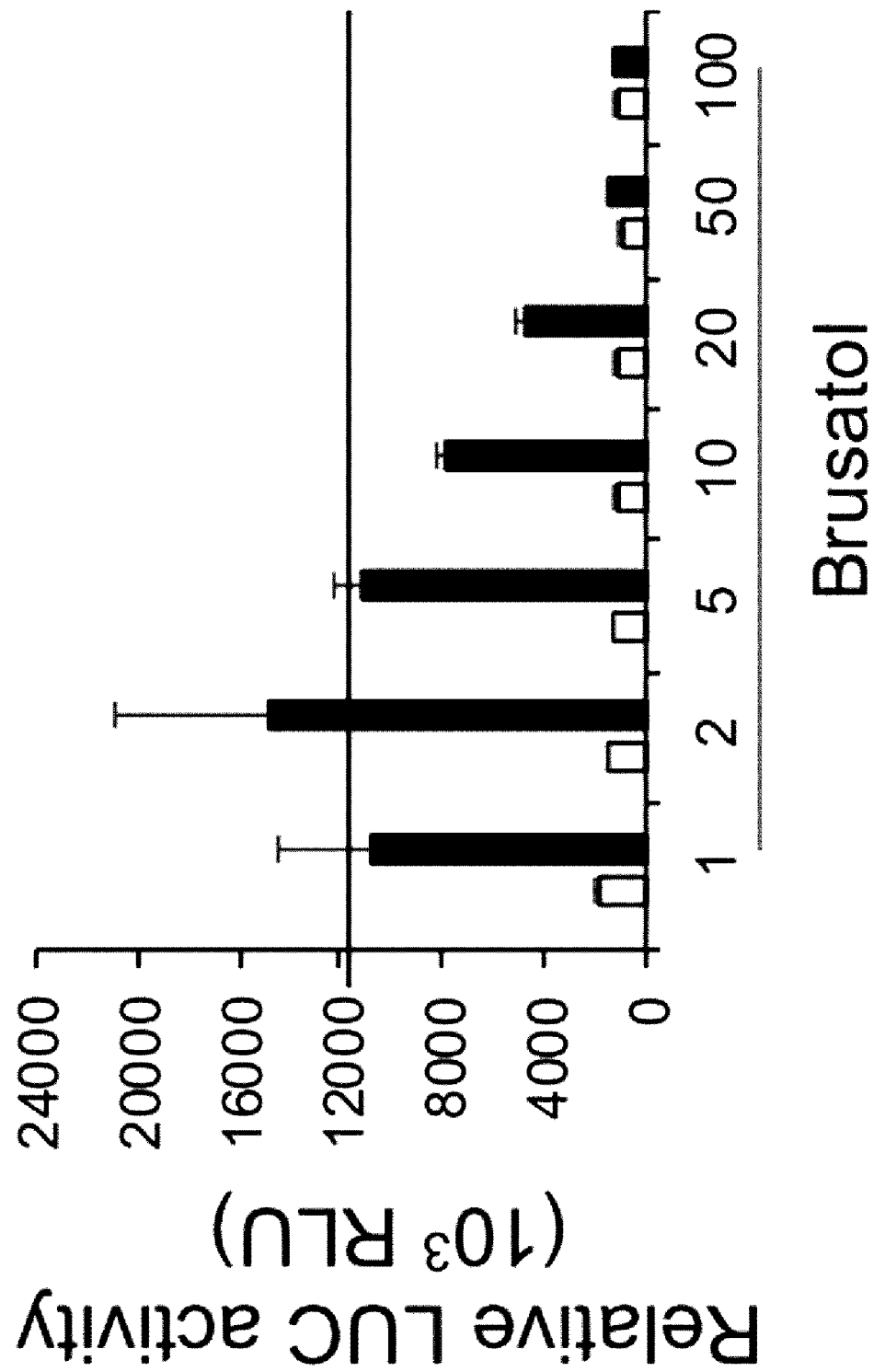
FIG. 4d is a graph showing inhibitory effects of brusatol on hormone-dependent AR transcriptional activity of the androgen-dependent prostate cancer cell line LNCaP, along with analyzed $IC_{50}$ values, according to an embodiment of the present disclosure.
Figure 4E:
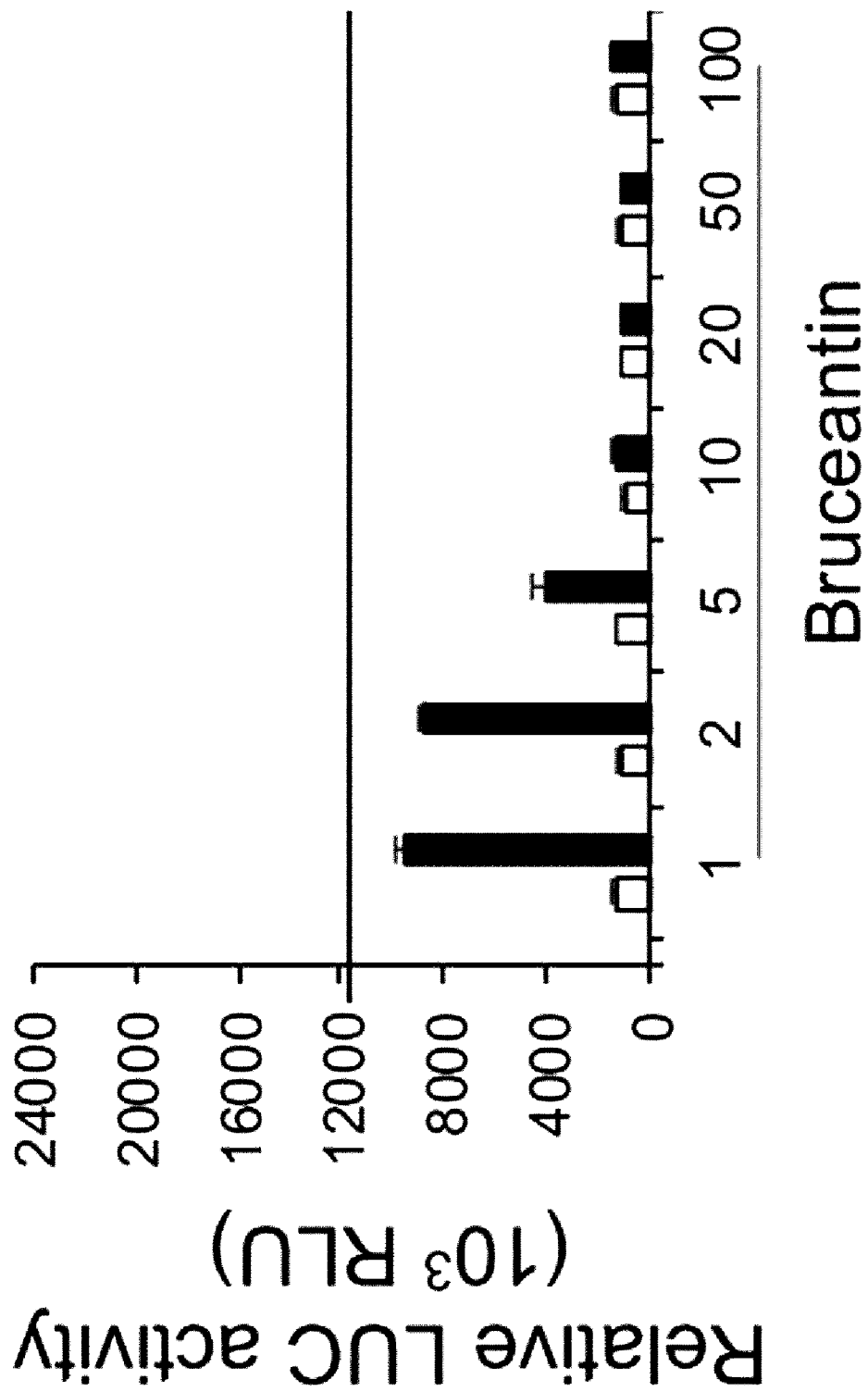
FIG. 4e is a graph showing inhibitory effects of bruceantin on hormone-dependent AR transcriptional activity of the androgen-dependent prostate cancer cell line LNCaP, along with analyzed $IC_{50}$ values, according to an embodiment of the present disclosure.

In brief, 22RV1 cells were transfected with an MMTV-LUC reporter and treated with various drugs at 7 concentrations ranging from 1 nM to 100 nM for each drug according to the presence and absence of the androgen hormone DHT (DHT+, conditions for measuring AR transcriptional activity; DHT−, condition for measuring AR-V7 transcriptional activity), followed by analyzing inhibitory activity against AR and AR-V7 transcriptional activity and measuring IC$_{50}$. The results are depicted in FIGS. 3a and 3b and summarized in Table 4.

TABLE 4

| IC$_{50}$ (nM) | ailanthone | bruceine A | brusatol | bruceantin |
|---|---|---|---|---|
| DHT− | 35.45 | 14.32 | 14.04 | 3.14 |
| DHT+ | 19.78 | 9.45 | 6.23 | 2.08 |

In addition, LNCaP cells were transfected with an MMTV-LUC reporter and treated with various drugs at 7 concentrations ranging from 1 nM to 100 nM for each drug according to the presence and absence of the androgen hormone DHT, followed by analyzing inhibition against hormone-dependent AR transcriptional activity and measuring IC$_{50}$. The results are depicted in FIGS. 4a to 4e and summarized in Table 5.

TABLE 5

| IC$_{50}$ (nM) | Enzalutamide | Ailanthone | Bruceine A | Brusatol | Bruceantin |
|---|---|---|---|---|---|
| DHT+ | 152.90 | 40.83 | 15.03 | 11.74 | 2.05 |

As can be understood from the data of FIGS. 3a to 4e and Tables 4 and 5, bruceantin, brusatol, and bruceine A all exhibited activity as more potent inhibitors against AR/AR-V7 transcriptional activity in both CRPC 22RV1 cells and androgen-dependent LNCaP cells than ailanthone.

Example 3. Cell Growth Inhibiting Activity and IC$_{50}$ Assay

The selected quassinoids bruceine A, brusatol, and bruceantin, and the reference compounds enzalutamide and ailanthone were assayed for inhibitory activity against 22RV1 cell growth by MTT.

In brief, 22RV1 cells were seeded at a density of 1×10$^4$ cells/well into 96-well plates and treated with each drug at 6 concentrations ranging from 5 nM to 200 nM for 72 hours. Afterwards, an MTT dye solution and a solubilization solution/stop mix were added according to an MTT assay method, followed by reading absorbance at 570 nm to analyze cell viability and IC$_{50}$. The data are depicted in FIG. 5 and summarized in Table 6.

TABLE 6

| IC$_{50}$ ENZ | ailanthone | bruceine A | brusatol | bruceantin |
|---|---|---|---|---|
| ND | 33.50 | 16.48 | 15.12 | 2.07 |

Figure 5:
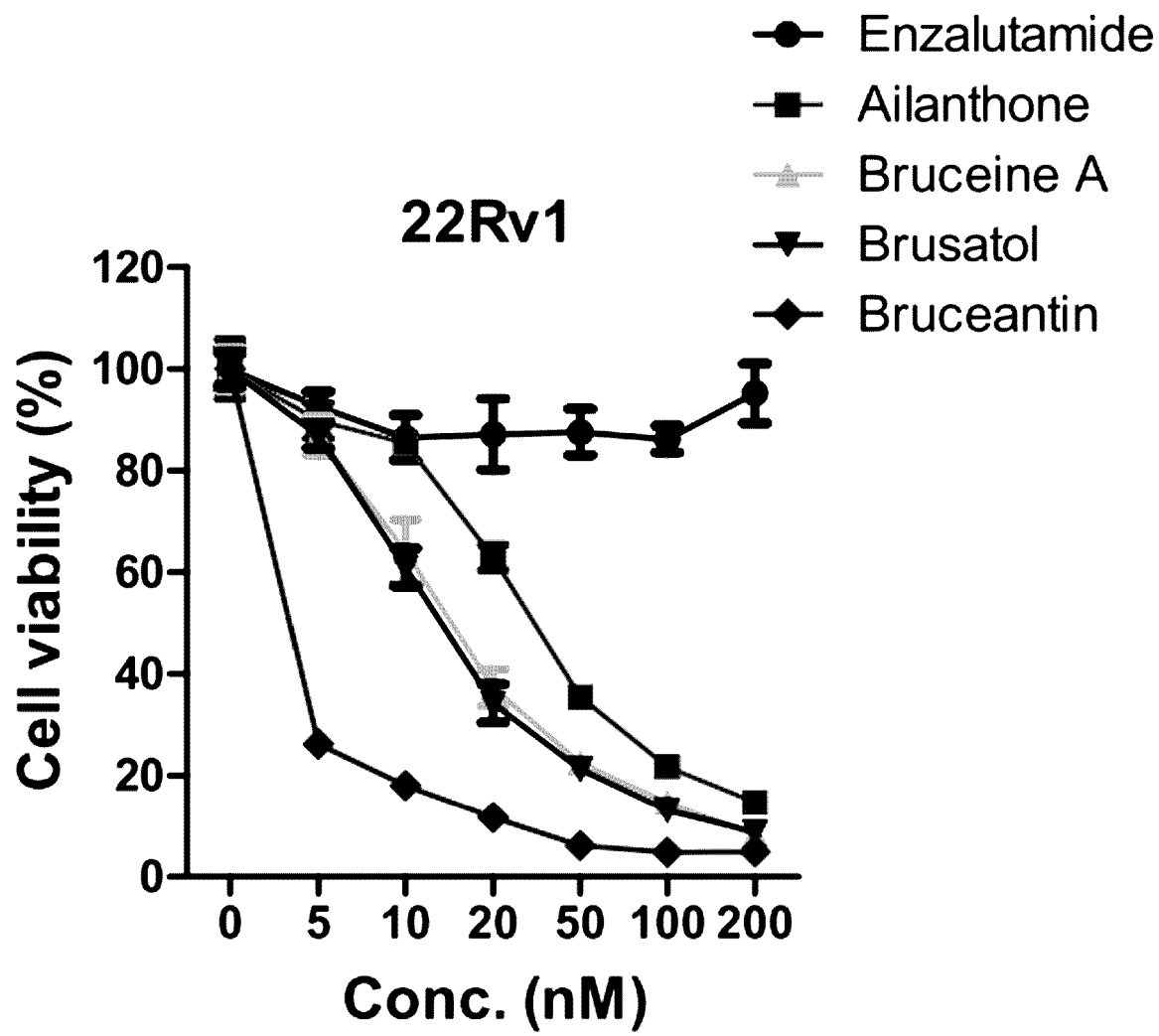
FIG. 5 is a graph showing inhibitory effects of the selected quassinoids and the reference compounds enzalutamide and ailanthone on cell growth of the CRPC cell line 22RV1, along with analyzed $IC_{50}$ values, according to an embodiment of the present disclosure.

As can be seen in FIG. 5 and Table 6, bruceantin was identified to have 16-fold more potent inhibitory activity against CRPC cell growth than ailanthone.

Example 4. Assay for Inhibitory Activity of Bruceantin Against Cell Growth

Bruceantin was analyzed for inhibitory activity against cell growth of normal prostate cells (RWPE-1), AR-negative prostate cancer cells (DU145, PC3), AR-positive hormone-dependent prostate cancer cells (LNCaP, C4-2B), AR- & AR-V7-positive castration-resistant prostate cancer cells (C4-2B-MDVR and 22RV1) by an MTT assay method.

In brief, the cell lines were each seeded at a density of 1×10$^4$ cells/well into 96-well plates and incubated with each of the drugs at three concentrations ranging from 1 nM to 5 nM for 72 hours. Afterwards, an MTT dye solution and a solubilization solution/stop mix were added according to an MTT assay method, followed by reading absorbance at 570 nm to analyze cell viability. The data are depicted in FIG. 6.

Figure 6:
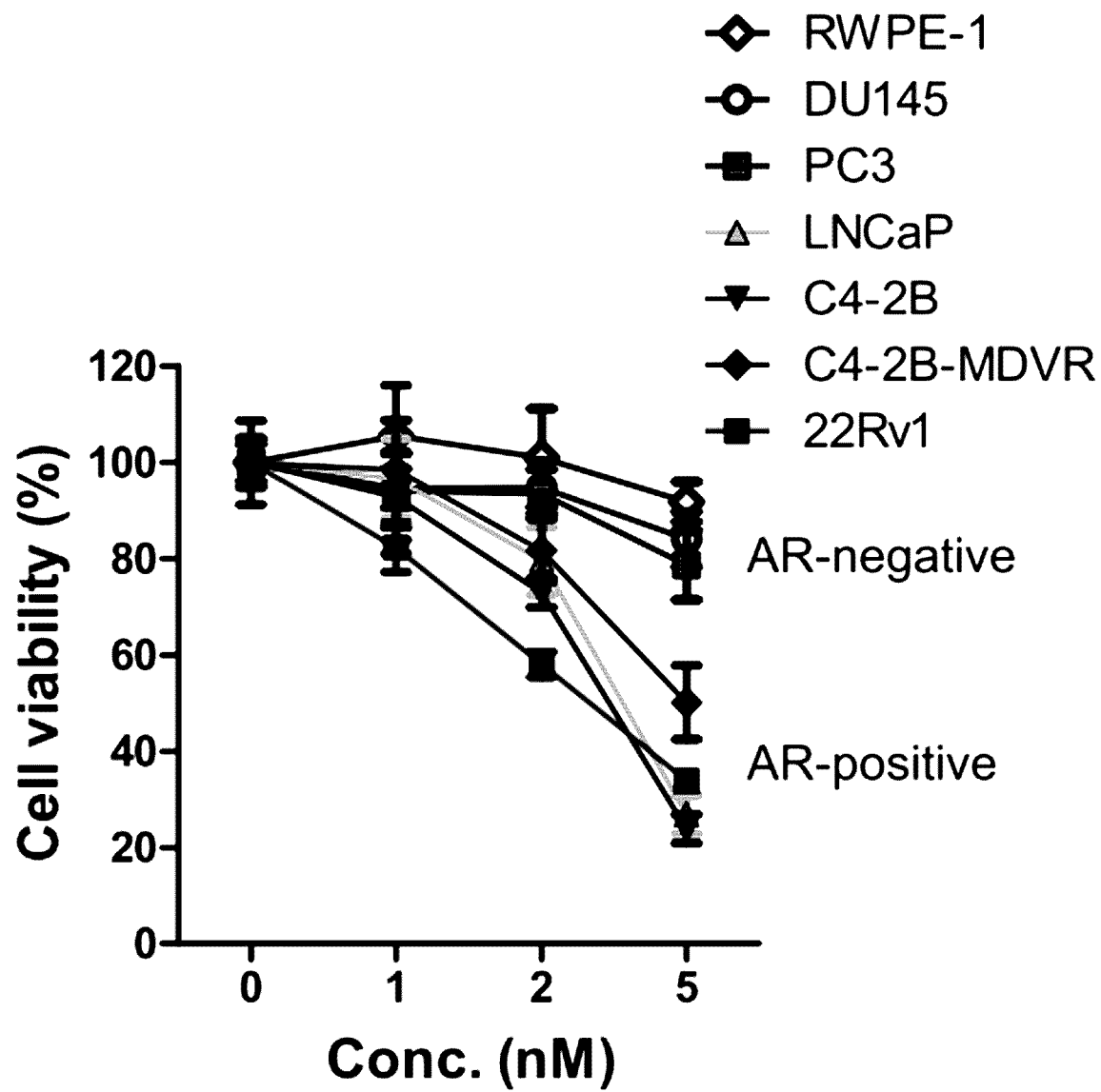
FIG. 6 is a graph showing inhibitory activity assay results of the selected bruceantin against cell growth of normal prostate cells and various prostate cancer cells according to an embodiment of the present disclosure.

As can be seen in FIG. 6, bruceantin was found to have inhibitory activity specifically against AR- and AR-V7-positive prostate cancer cells than normal prostate cells and AR-negative prostate cancer cells.

The data imply that bruceantin specifically targets both AR and AR-V7 and is sufficiently worth developing as a therapeutic agent for use for targeting the progressive prostate cancer AR/AR-V7-positive CRPC as well as AR-positive prostate cancer in the early stage.

Example 5. Inhibitory Activity of Bruceantin Against Tumor Growth

While being subcutaneously injected with bruceantin at a dose of 1 mg/kg/every 3 days, 22RV1-xenografted mouse models were monitored for inhibitory effects on tumor growth and body weights. The results are depicted in FIGS. 7a to 8b and summarized in Tables 7 to 10.

TABLE 7

| Tumor | DMSO | | 1 mg/kg | |
|---|---|---|---|---|
| Day | ave | stdev | ave | stdev |
| 0 | 65.6 | 17.0 | 57.5 | 11.3 |
| 3 | 72.8 | 14.9 | 81.7 | 27.1 |
| 6 | 166.0 | 58.5 | 161.6 | 55.4 |
| 9 | 266.6 | 87.2 | 250.2 | 135.4 |
| 12 | 546.6 | 258.9 | 428.0 | 152.4 |
| 15 | 733.4 | 172.1 | 676.3 | 181.8 |
| 18 | 1167.3 | 224.6 | 895.7 | 273.0 |
| 21 | 1522.6 | 323.1 | 938.5 | 320.6 |
| 24 | 1908.3 | 127.7 | 1005.7 | 136.0 |

TABLE 8

| Weight | DMSO | | 1 mg/kg | |
|---|---|---|---|---|
| Day | ave | stdev | ave | stdev |
| 0 | 19.8 | 1.1 | 20.0 | 2.3 |
| 3 | 20.0 | 1.0 | 19.8 | 2.2 |

TABLE 8-continued

| Weight | DMSO | | 1 mg/kg | |
|---|---|---|---|---|
| Day | ave | stdev | ave | stdev |
| 6 | 20.4 | 0.5 | 20.0 | 2.1 |
| 9 | 20.4 | 0.9 | 20.6 | 2.6 |
| 12 | 20.2 | 0.8 | 20.2 | 2.7 |
| 15 | 20.6 | 0.9 | 19.8 | 2.8 |
| 18 | 21.2 | 0.8 | 19.6 | 3.1 |
| 21 | 19.8 | 0.8 | 19.4 | 2.3 |
| 24 | 20.0 | 1.2 | 18.6 | 3.1 |

TABLE 9

| Weight | DMSO | | 0.25 mg/kg | | 0.5 mg/kg | | 1 mg/kg | |
|---|---|---|---|---|---|---|---|---|
| days | ave | stdev | ave | stdev | ave | stdev | ave | stdev |
| 0 | 16.8 | 1.3 | 16.0 | 1.8 | 15.8 | 1.5 | 16.5 | 1.0 |
| 3 | 16.8 | 1.0 | 16.8 | 1.3 | 16.3 | 1.5 | 16.8 | 1.3 |
| 6 | 17.0 | 1.4 | 17.3 | 1.3 | 16.5 | 1.7 | 17.3 | 1.0 |
| 9 | 17.3 | 1.3 | 18.3 | 1.3 | 18.3 | 1.3 | 18.5 | 0.6 |
| 12 | 17.8 | 1.5 | 20.0 | 1.4 | 18.0 | 1.4 | 19.8 | 1.5 |
| 15 | 19.0 | 2.2 | 21.5 | 0.6 | 18.7 | 2.5 | 19.5 | 2.6 |
| 18 | 20.0 | 1.8 | 22.0 | 0.8 | 19.7 | 2.5 | 21.0 | 2.2 |
| 21 | 19.5 | 1.9 | 22.0 | 1.2 | 19.7 | 3.1 | 21.5 | 1.9 |
| 24 | 19.8 | 1.7 | 22.5 | 0.6 | 20.7 | 2.5 | 21.8 | 2.2 |
| 27 | 20.5 | 1.9 | 22.5 | 0.6 | 21.0 | 3.0 | 22.5 | 1.9 |

TABLE 10

| AST/ALT | ave | stdev |
|---|---|---|
| DMSO | 2.4 | 1.4 |
| 0.25 mg/kg | 2.3 | 0.6 |
| 0.5 mg/kg | 2.5 | 0.9 |
| 1 mg/kg | 3.3 | 0.6 |

Figure 7A:
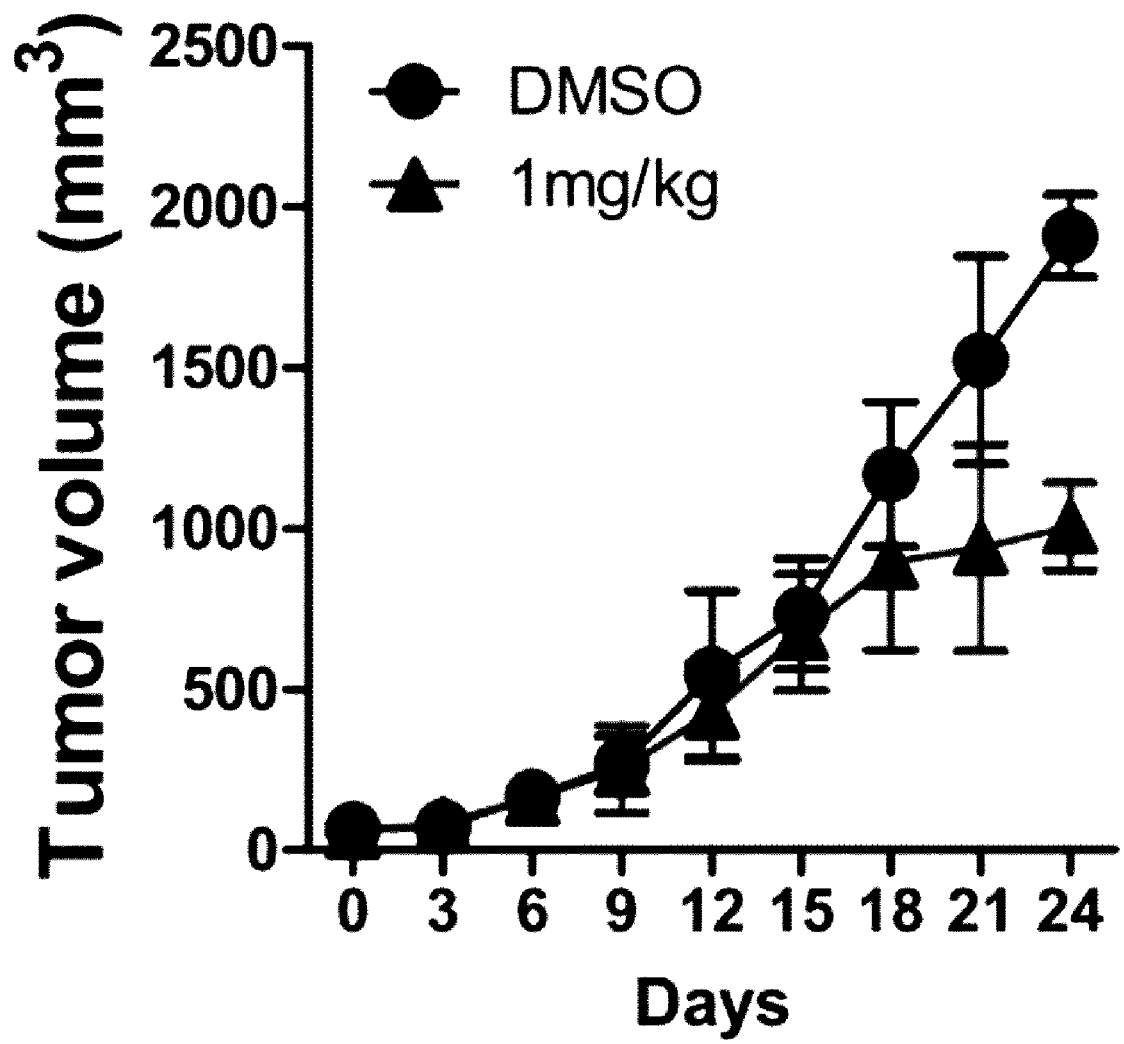
FIG. 7a is a graph showing inhibitory activity assay results of bruceantin against tumor growth in mouse models xenografted with the castration-resistant prostate cancer cell line 22RV1 according to an embodiment of the present disclosure.
Figure 7B:
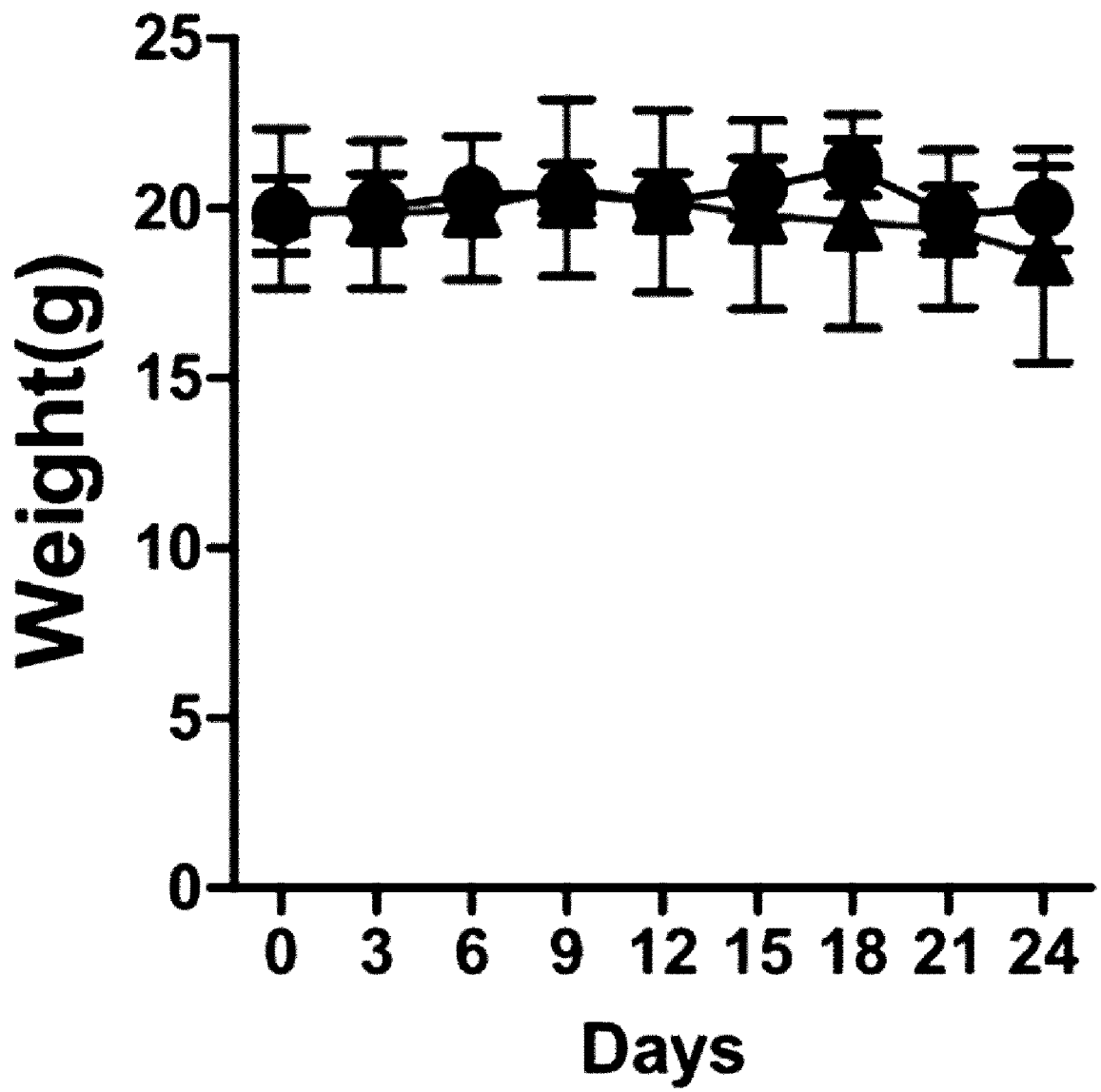
FIG. 7b is a graph showing body weight change patterns analyzed with the administration of bruceantin to mouse models xenografted with the castration-resistant prostate cancer cell line 22RV1 according to an embodiment of the present disclosure.
Figure 7C:
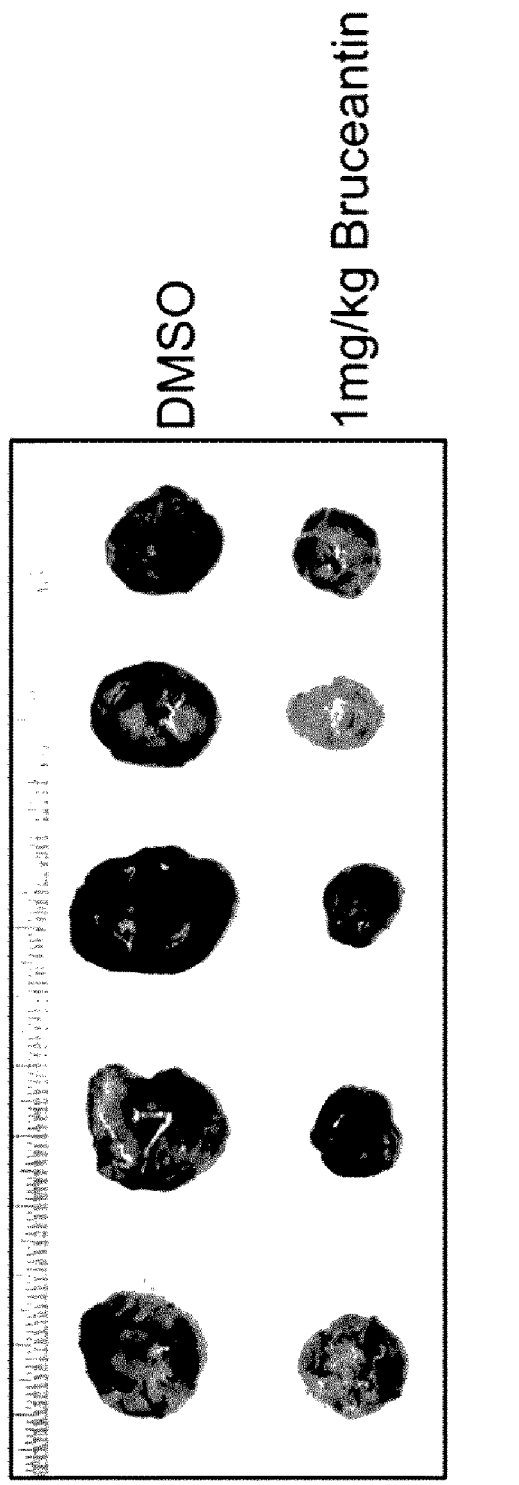
FIG. 7c is an image showing assay results for inhibitory activity of bruceantin against tumor growth in mouse models xenografted with the castration-resistant prostate cancer cell line 22RV1 according to an embodiment of the present disclosure.

As can be seen in FIGS. 7a to 7c, CRPC mouse xenograft model experiments were performed using nude mice and 22RV1 cells, identifying that a dose of 1 mg/kg of bruceantin can effectively inhibit in vivo tumor growth of CRPC cells.

Figure 8A:
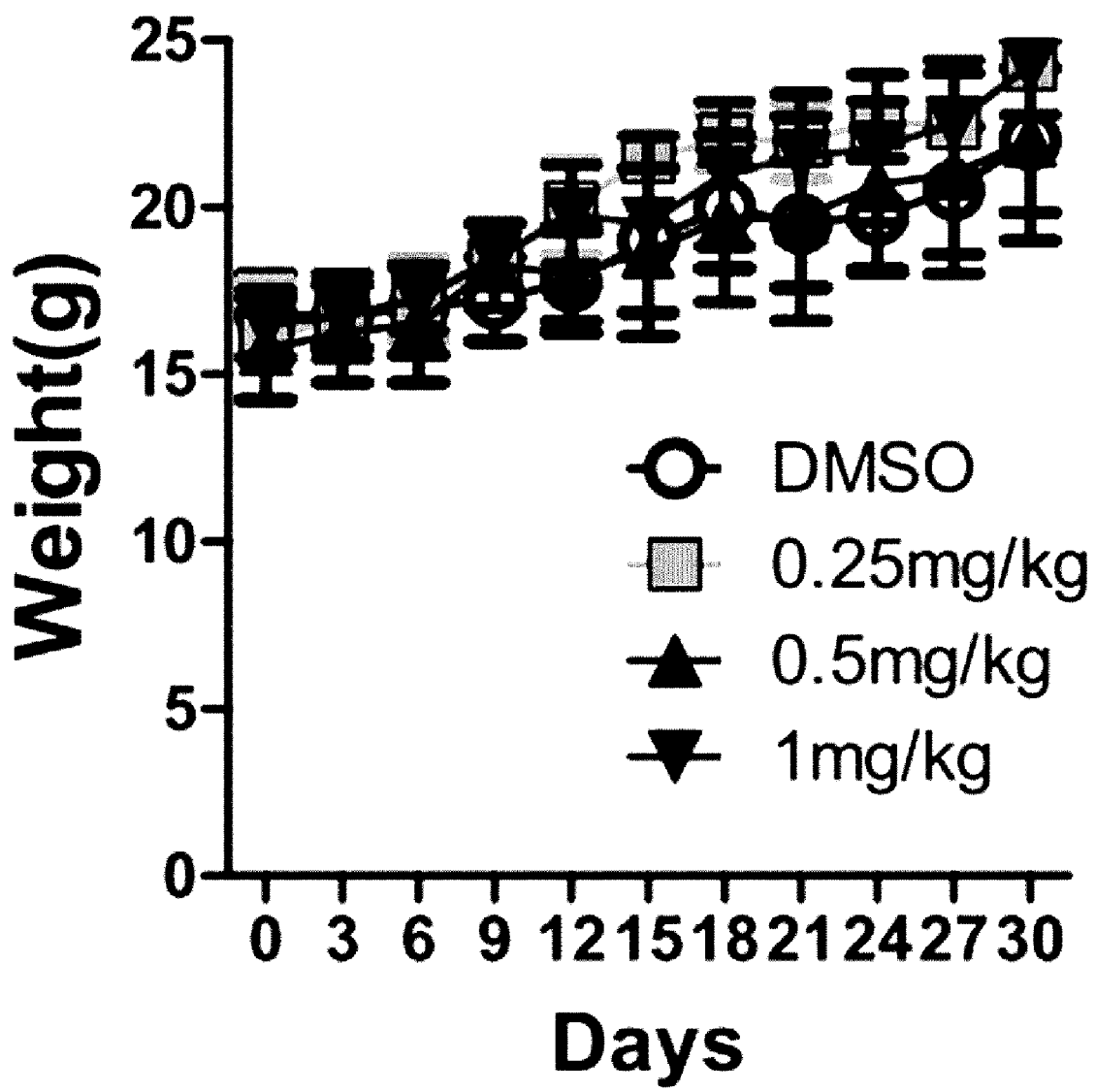
FIG. 8a shows body weight changes plotted against time by doses of bruceantin subcutaneously injected to mice according to an embodiment of the present disclosure.
Figure 8B:
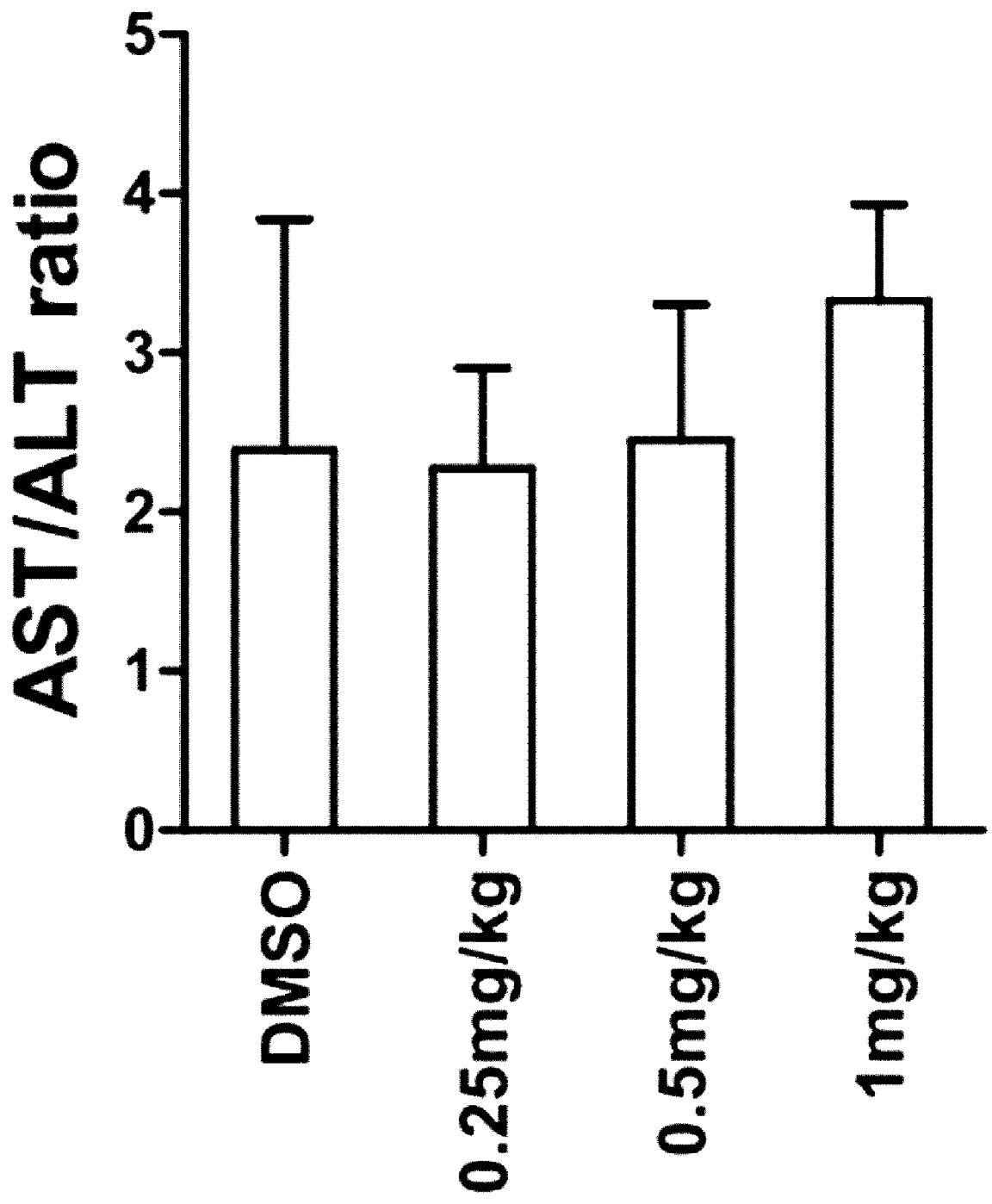
FIG. 8b is a graph showing changes in blood AST/ALT ratio with doses of bruceantin subcutaneously injected to mice according to an embodiment of the present disclosure.

In addition, as shown in FIGS. 8a and 8b, a dose of 1 mg/kg of bruceantin was found to have no effect on weights of the mice nor to cause hepatotoxicity.

Figure 9A:
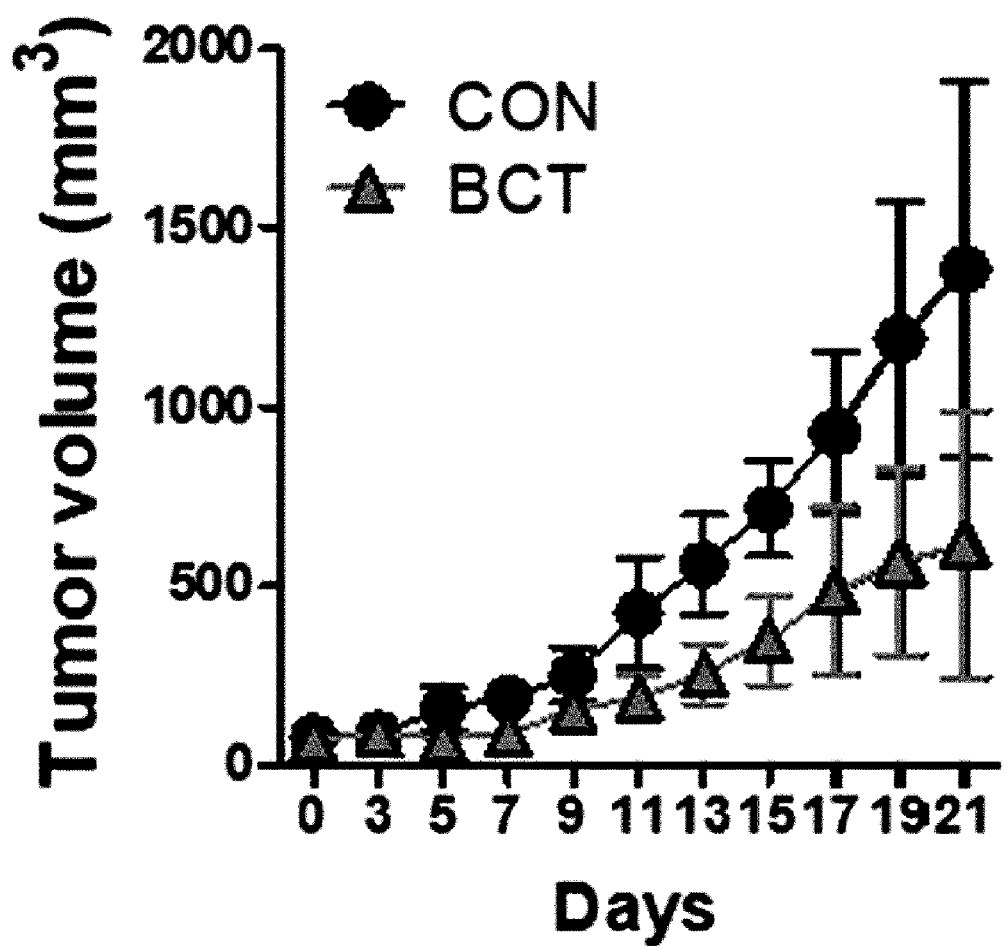
FIG. 9a is a graph showing inhibitory effects of orally administered bruceantin on tumor growth observed in CRPC xenograft mouse models accordance to an embodiment of the present disclosure.
Figure 9B:
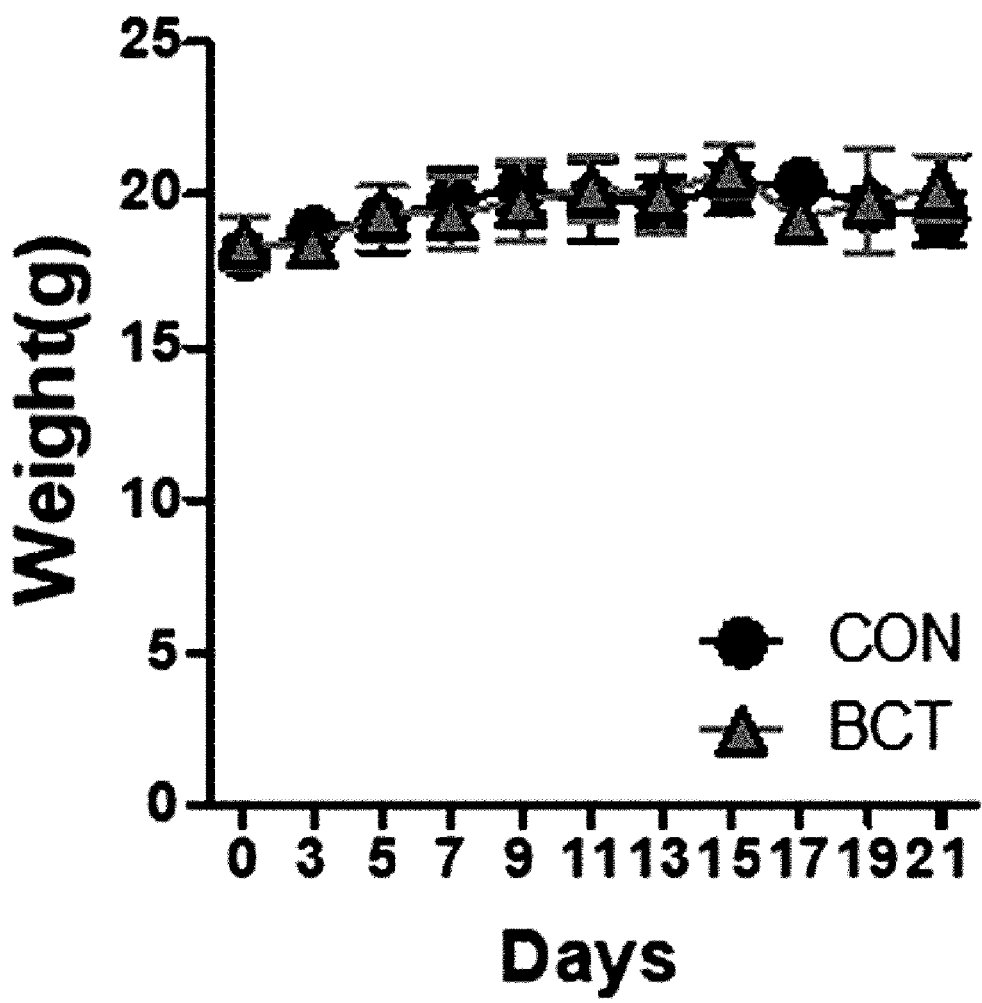
FIG. 9b is a graph showing body weight changes with orally administered bruceantin observed in CRPC xenograft mouse models accordance to an embodiment of the present disclosure.

Example 6. Assay for Pharmaceutical Efficacy of Orally Administered Bruceantin in CRPC Xenograft Mouse Model In mouse models xenografted with the castration-resistant prostate cancer (CRPC) cell line 22RV1, bruceantin was analyzed for inhibitory effect on tumor growth. To this end, bruceantin was orally administered at a dose of 2 mg/kg/every 2 days to 22RV1 xenograft mouse models during which inhibition effects on tumor growth and body weights were monitored. The results are depicted in FIGS. 9a and 9b and Tables 11 and 12.

TABLE 11

| Tumor | CON | | BCT | |
|---|---|---|---|---|
| Day | ave | stdev | ave | stdev |
| 0 | 78.588 | 24.6579 | 73.0453 | 34.77342 |
| 3 | 86.8976 | 22.71908 | 89.5358 | 20.76171 |
| 5 | 158.5855 | 61.27517 | 75.35 | 7.167657 |
| 7 | 187.565 | 47.10095 | 88.811 | 17.01849 |

TABLE 11-continued

| Tumor | CON | | BCT | |
|---|---|---|---|---|
| Day | ave | stdev | ave | stdev |
| 9 | 251.8748 | 75.00192 | 157.6571 | 14.79558 |
| 11 | 425.1111 | 155.4311 | 189.9515 | 62.37772 |
| 13 | 560.3242 | 139.3798 | 256.5573 | 83.592 |
| 15 | 716.193 | 133.8083 | 348.6721 | 122.5188 |
| 17 | 929.6541 | 224.8357 | 485.1394 | 233.2228 |
| 19 | 1191.658 | 383.5053 | 567.0807 | 258.086 |
| 21 | 1383.706 | 524.9933 | 616.549 | 371.1777 |

TABLE 12

| Weight | CON | | BCT | |
|---|---|---|---|---|
| Day | ave | stdev | ave | stdev |
| 0 | 18 | 0.707107 | 18.4 | 0.894427 |
| 3 | 18.8 | 0.447214 | 18.4 | 0.547723 |
| 5 | 19.2 | 1.095445 | 19.4 | 0.894427 |
| 7 | 19.8 | 1.095445 | 19.4 | 1.140175 |
| 9 | 20.2 | 0.83666 | 19.8 | 1.30384 |
| 11 | 19.8 | 1.30384 | 20.2 | 1.095445 |
| 13 | 19.8 | 0.83666 | 20 | 1.224745 |
| 15 | 20.2 | 0.83666 | 20.8 | 0.83666 |
| 17 | 20.4 | 0.547723 | 19.2 | 0.447214 |
| 19 | 19.6 | 0.547723 | 19.8 | 1.643168 |
| 21 | 19.2 | 0.83666 | 20.2 | 1.095445 |

As can be seen in FIGS. 9a and 9b and Tables 11 and 12, bruceantin was found to effectively inhibit tumor growth without changing the body weight.

Figure 10:
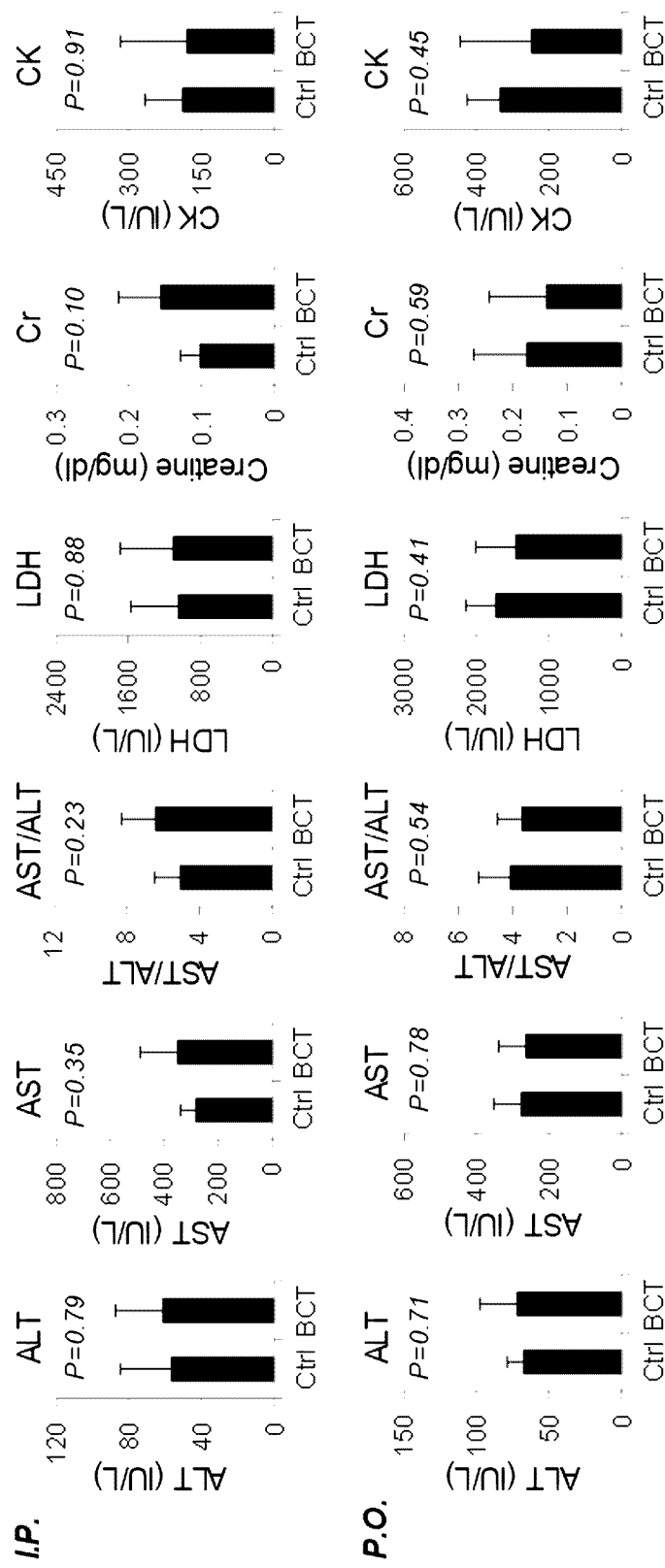
FIG. 10 shows graphs of hematobiochemical toxicity assay results in mice to which bruceantin has been subcutaneously and orally administered according to an embodiment of the present disclosure.

Example 7. Hematobiochemical Toxicity Assay of Bruceantin in Subcutaneously Injected Mouse Bloods from mice after subcutaneous injection and oral administration of bruceantin thereto were quantitatively analyzed for toxicity biomarkers. Briefly, in order to analyze toxicity of bruceantin in vivo, bloods from 22RV1 xenograft mouse models were measured for various serological indices after subcutaneous injection at a dose of 1 mg/kg/every 3 days (IP) and oral administration at a dose of 2 mg/kg/every 2 days (p.o.), and the results are depicted in FIG. 10 and summarized in Table 13.

ALT: Alanine transaminase
AST: Aspartate transaminase
LDH: Lactate dehydrogenase
CR: Creatinine
CPK: Creatine phosphokinase

TABLE 13

| | | Ctrl | | BCT | |
|---|---|---|---|---|---|
| | | ave | stdev | ave | stdev |
| I.P. | ALT | 56.4 | 28.01428 | 61.2 | 26.03267 |
| | AST | 283.8 | 56.82605 | 351 | 139.4758 |
| | AST/ALT | 5.047834 | 1.41858 | 6.408889 | 1.873642 |
| | LDH | 1045.2 | 526.4534 | 1098.6 | 587.5575 |
| | Cr | 0.102 | 0.026833 | 0.156 | 0.057706 |
| | CK | 188.4 | 78.21317 | 180 | 136.8539 |
| P.O. | ALT | 67.2 | 11.54123 | 72 | 25.71964 |
| | AST | 277.2 | 75.07796 | 263.4 | 75.34122 |
| | AST/ALT | 4.081746 | 1.167746 | 3.657719 | 0.898977 |
| | LDH | 1724.4 | 424.4889 | 1456.8 | 546.8178 |
| | Cr | 0.174 | 0.098133 | 0.138 | 0.105214 |
| | CK | 334.5 | 91.7006 | 247.5 | 195.7217 |

As can be seen in FIG. 10 and Table 13, bruceantin was observed to exhibit no toxicity on blood indices, compared to the control vehicle.

Example 8. Anatomical and Histological Toxicity Assay of Bruceantin in Subcutaneously Injected Mouse Anatomical and histological toxicity assays were performed on livers, kidneys and spleens from the mice subcutaneously injected with bruceantin. In order to analyze in vivo toxicity of bruceantin, liver, kidney, and spleen tissues from 22RV1 xenograft mouse models were analyzed after subcutaneous injection at a dose of 1 mg/kg/every 3 days, and the results are depicted in FIGS. 11a and 11b.

Figure 11A:
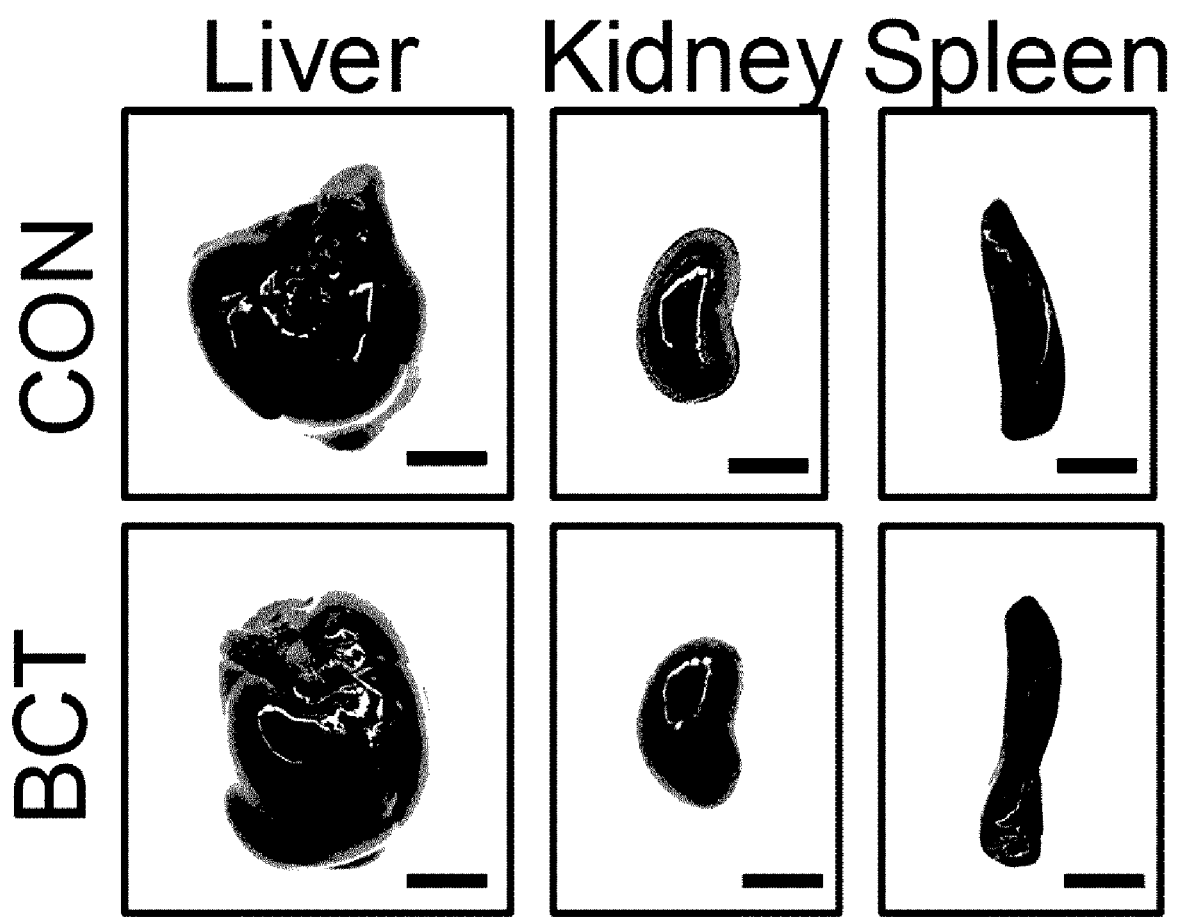
FIG. 11a shows images elucidating anatomical toxicity assay results in mice subcutaneously injected with bruceantin according to an embodiment of the present disclosure.
Figure 11B:
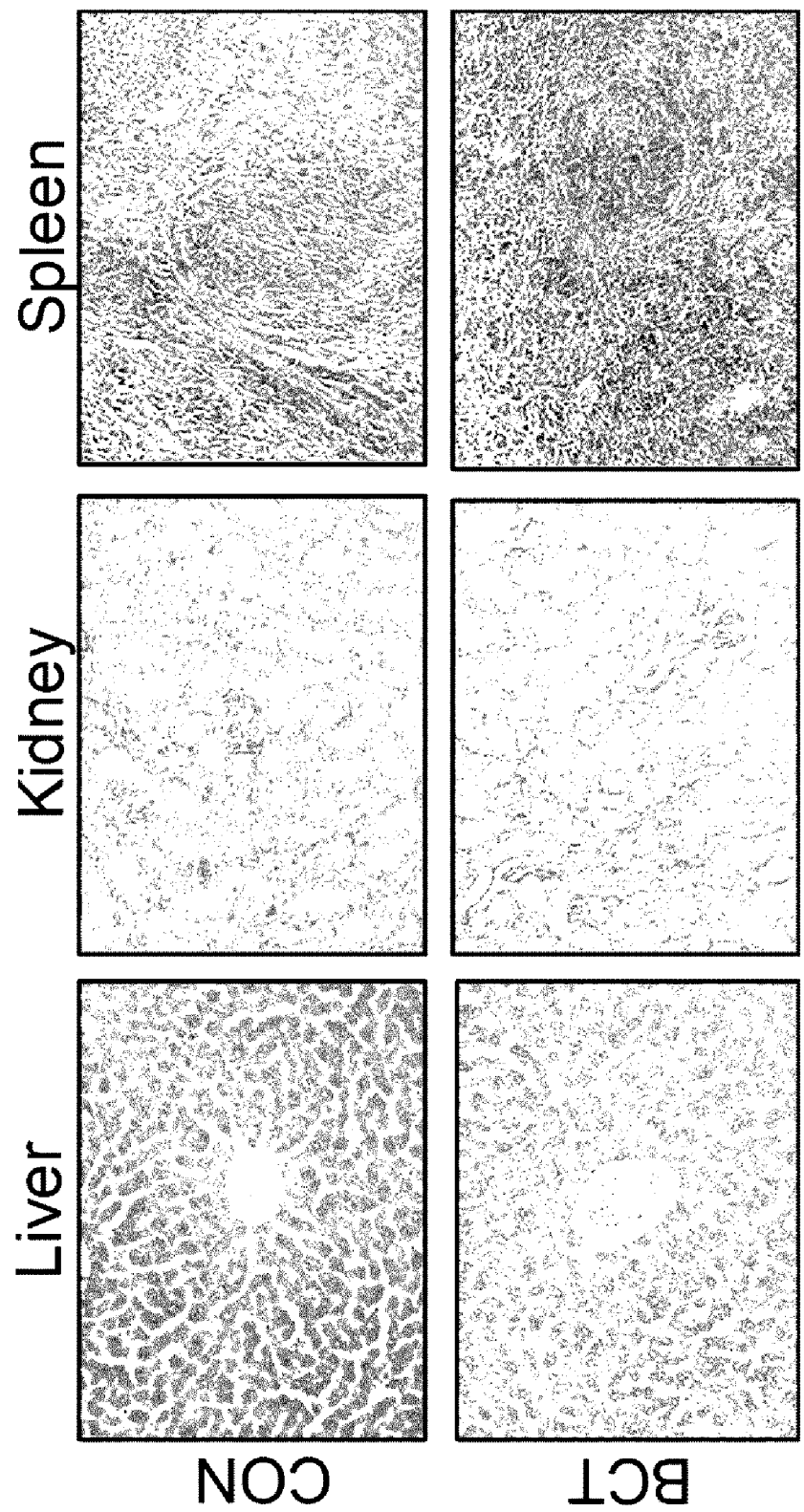
FIG. 11b shows images elucidating histological toxicity assay results in mice subcutaneously injected with bruceantin according to an embodiment of the present disclosure.

As can be seen in FIGS. 11a and 11b, bruceantin was found to show no morphological and histological changes (toxicity) in each tissue, compared to the control vehicle.

Example 9. Anatomical and Histological Toxicity Assay of Bruceantin in Orally Administered Mouse Anatomical and histological toxicity assays were performed on livers, kidneys and spleens from the mice to which bruceantin had been orally administered. In order to analyze in vivo toxicity of bruceantin, liver, kidney, and spleen tissues from 22RV1 xenograft mouse models were analyzed after oral administration at a dose of 2 mg/kg/every 2 days, and the results are depicted in FIGS. 12a and 12d.

Figure 12A:
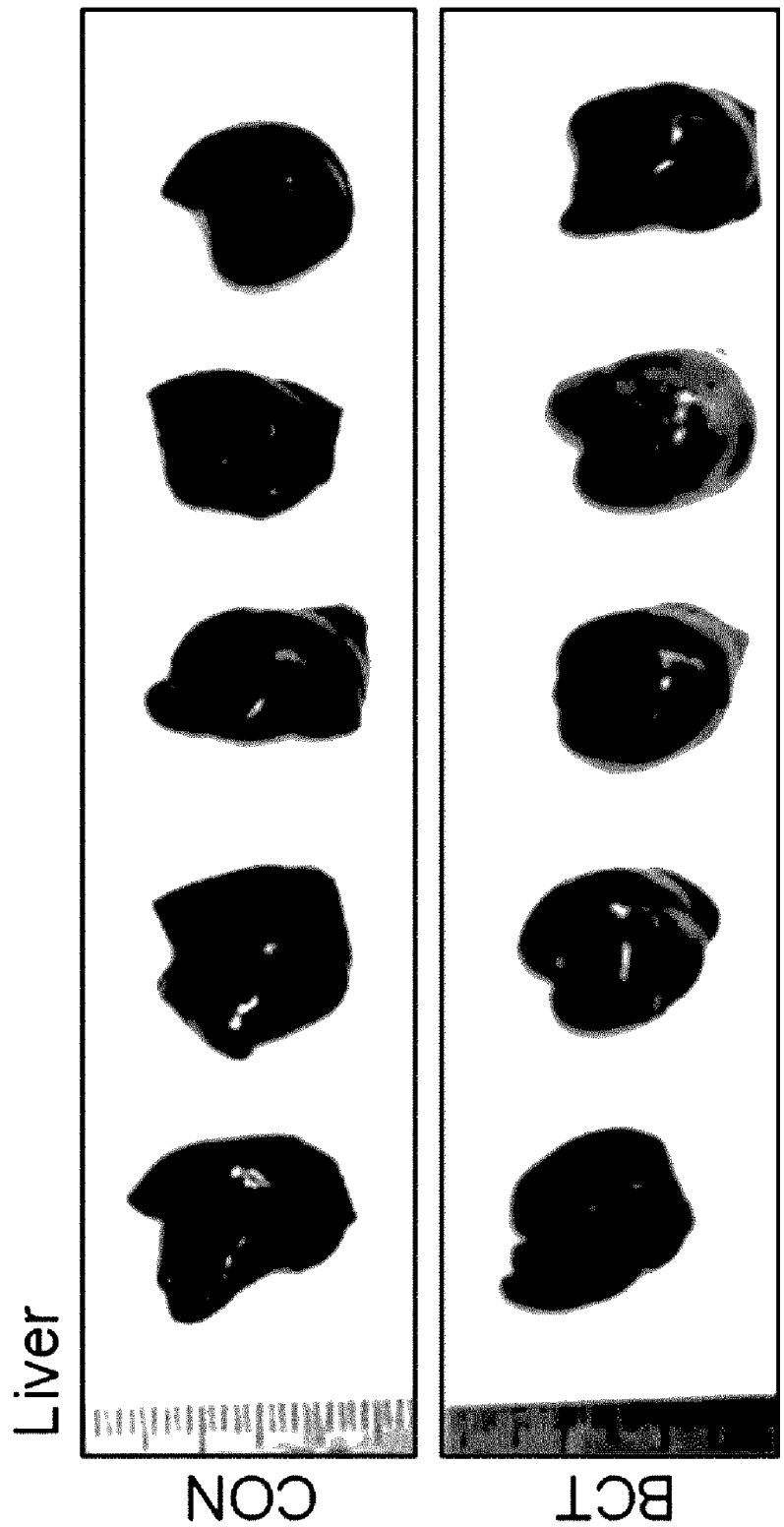
FIG. 12a shows images of anatomical toxicity assay results in livers from mice to which bruceantin has been orally administered according to an embodiment of the present disclosure.
Figure 12B:
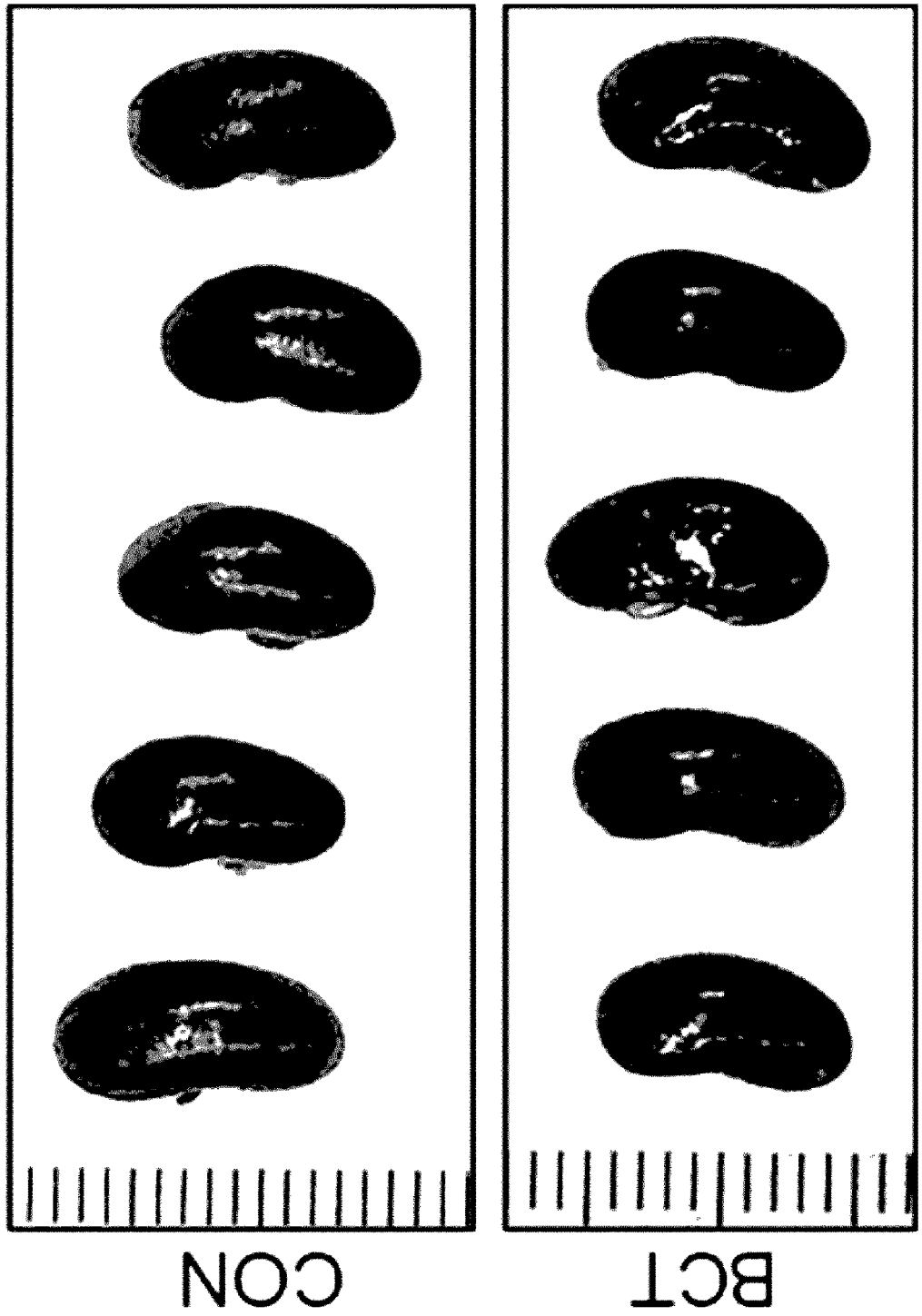
FIG. 12b shows images of anatomical toxicity assay results in kidneys from mice to which bruceantin has been orally administered according to an embodiment of the present disclosure.
Figure 12C:
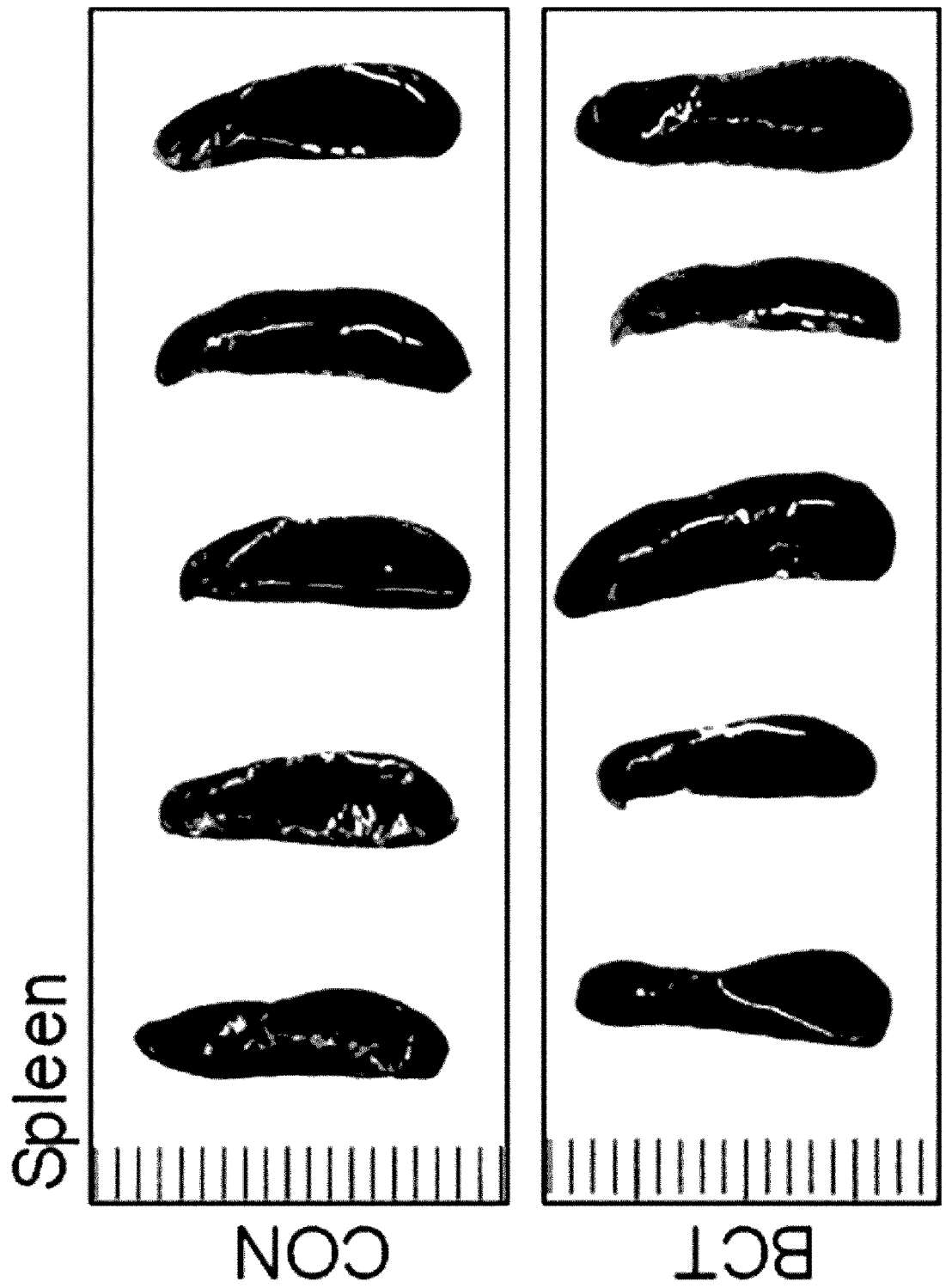
FIG. 12c shows images of anatomical toxicity assay results in spleens from mice to which bruceantin has been orally administered according to an embodiment of the present disclosure.
Figure 12D:
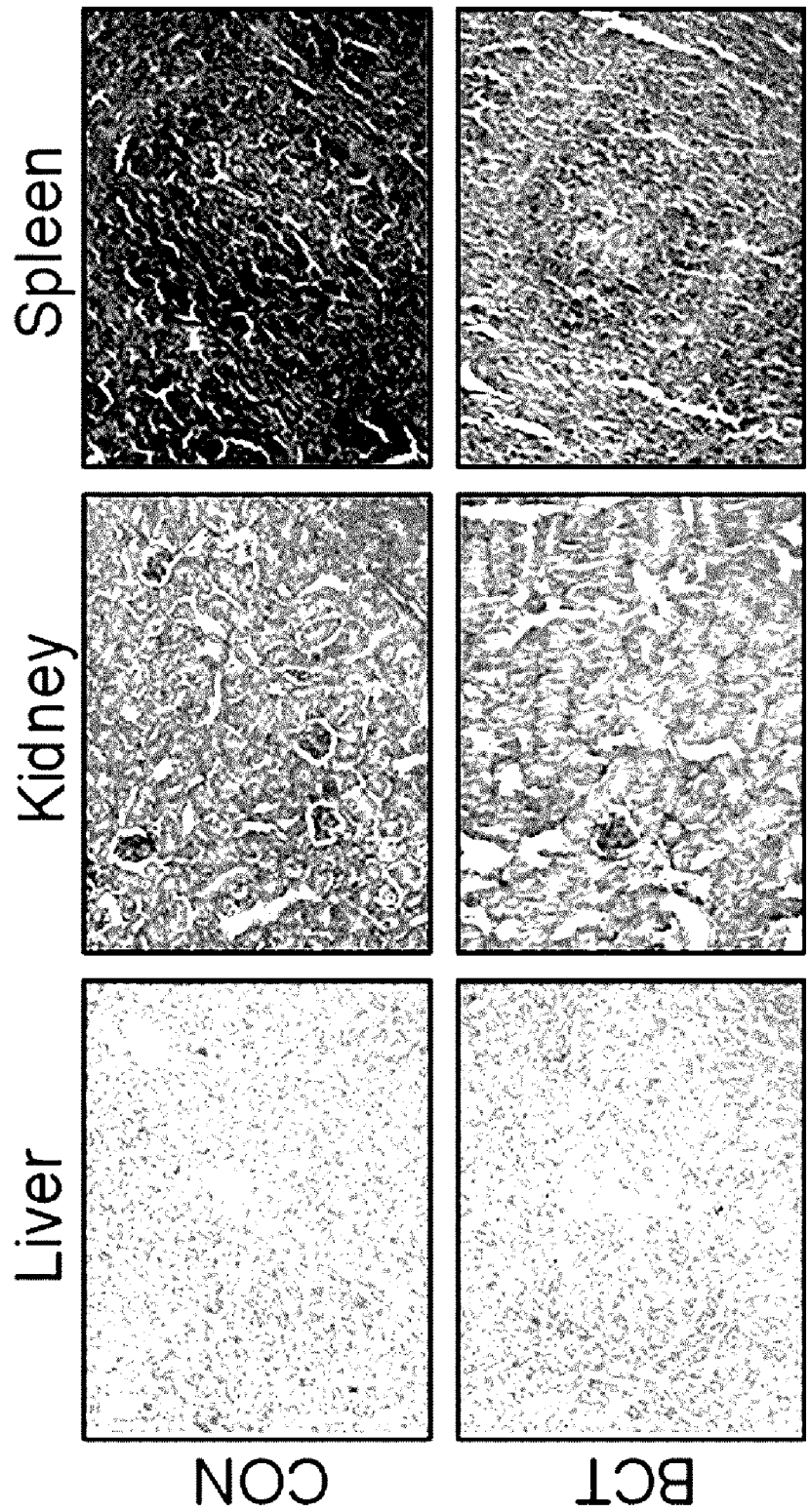
FIG. 12d shows images of histological toxicity assay results in mice to which bruceantin has been orally administered according to an embodiment of the present disclosure.

As can be seen in FIGS. 12a and 12d, bruceantin was found to show no morphological and histological changes (toxicity) in each tissue, compared to the control vehicle.

Example 10. Construction of CRPC Xenograft Metastasis Mouse Model

Figure 13:
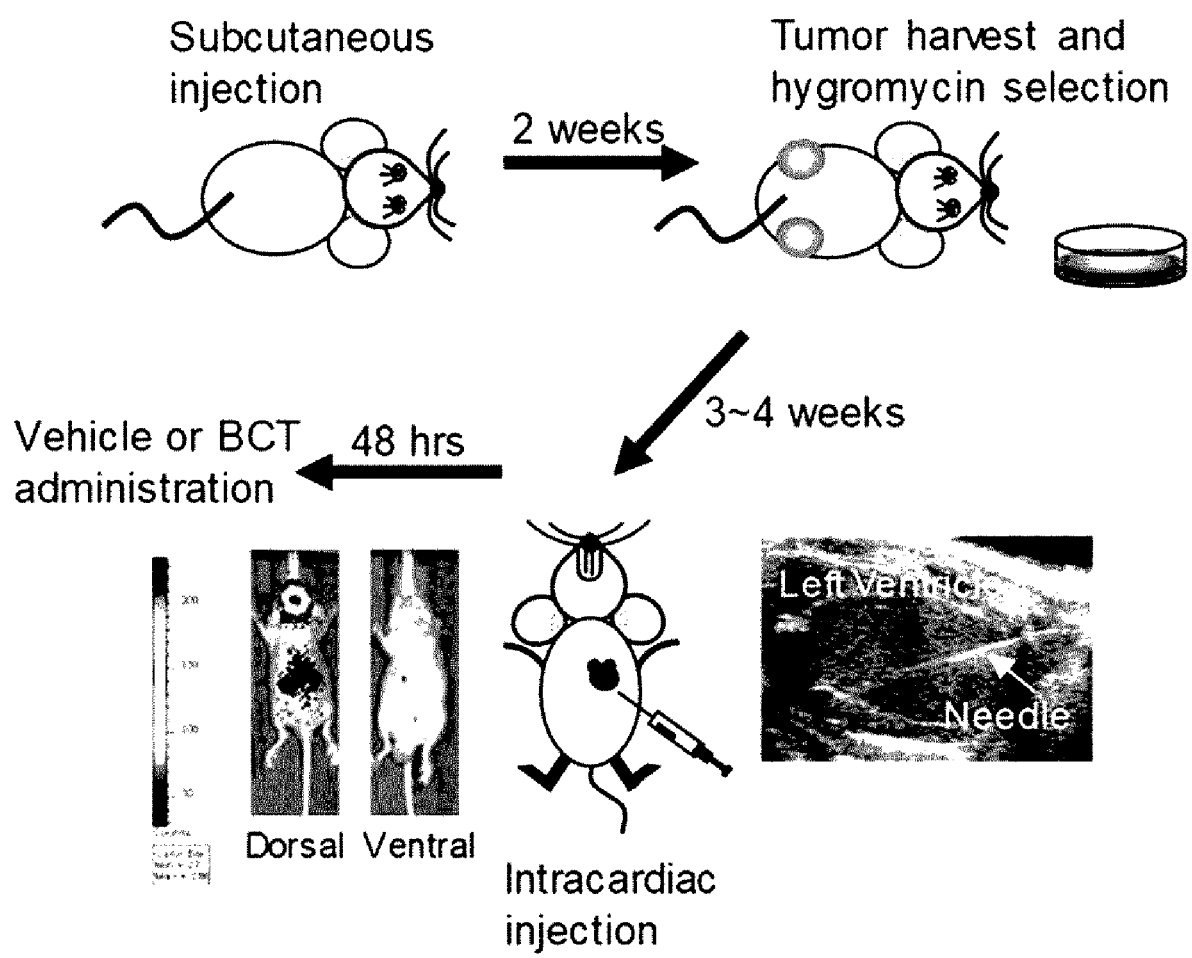
FIG. 13 is a schematic diagram illustrating the construction of a CRPC xenograft metastasis mouse model according to an embodiment of the present disclosure.

In order construct metastasis mouse models with the castration-resistant prostate cancer cell line 22RV1, the cells were subcutaneously injected into nude mice and the tumors was grown. Then, the tumors were harvested and injected into the left cardiac ventricle of nude mice to construct metastasis mouse models (see FIG. 13).

Example 11. Assay for Inhibitory Effect of Orally Administered Bruceantin on Metastasis in CRPC Xenograft Metastasis Mouse Model In the metastasis mouse models using the castration-resistant prostate cancer cell line 22RV1, bruceantin was analyzed for inhibitory effect on tumor metastasis and growth. In brief, the metastasis mice were monitored for inhibitory effects on tumor metastasis and growth and body weight while bruceantin was orally administered at a dose of 2 mg/kg/every 2 days thereto. The results are depicted in FIGS. 14a and 14b and Table 14.

TABLE 14

| weight | CON | | BCT | |
| --- | --- | --- | --- | --- |
| Day | ave | stdev | ave | stdev |
| 1 | 16.875 | 1.290994 | 16 | 1.195229 |
| 3 | 17.5 | 1.272418 | 16.75 | 1.164965 |
| 5 | 18.125 | 1.573592 | 17 | 1.309307 |
| 7 | 18.75 | 1.9518 | 17.25 | 1.28174 |
| 9 | 19.25 | 2.13809 | 18.125 | 1.125992 |
| 11 | 20.25 | 1.908627 | 19.375 | 1.407886 |
| 13 | 20.375 | 1.995531 | 19.625 | 1.505941 |
| 15 | 20.5 | 2.070197 | 19.625 | 1.30247 |
| 17 | 21.125 | 2.03101 | 20.375 | 1.505941 |
| 19 | 21.125 | 1.95941 | 20.375 | 1.187735 |
| 21 | 21.125 | 2.03101 | 20.5 | 1.195229 |
| 23 | 21.375 | 2.263846 | 20.625 | 1.505941 |
| 25 | 22 | 1.927248 | 21.25 | 0.886405 |
| 27 | 21.75 | 1.832251 | 21.125 | 1.246423 |
| 29 | 22.125 | 1.885092 | 21.625 | 1.505941 |
| 31 | 22.375 | 1.846812 | 21.625 | 1.30247 |
| 33 | 22.5 | 1.690309 | 21.625 | 1.30247 |
| 35 | 22.625 | 1.505941 | 21.75 | 1.752549 |

Figure 14A:
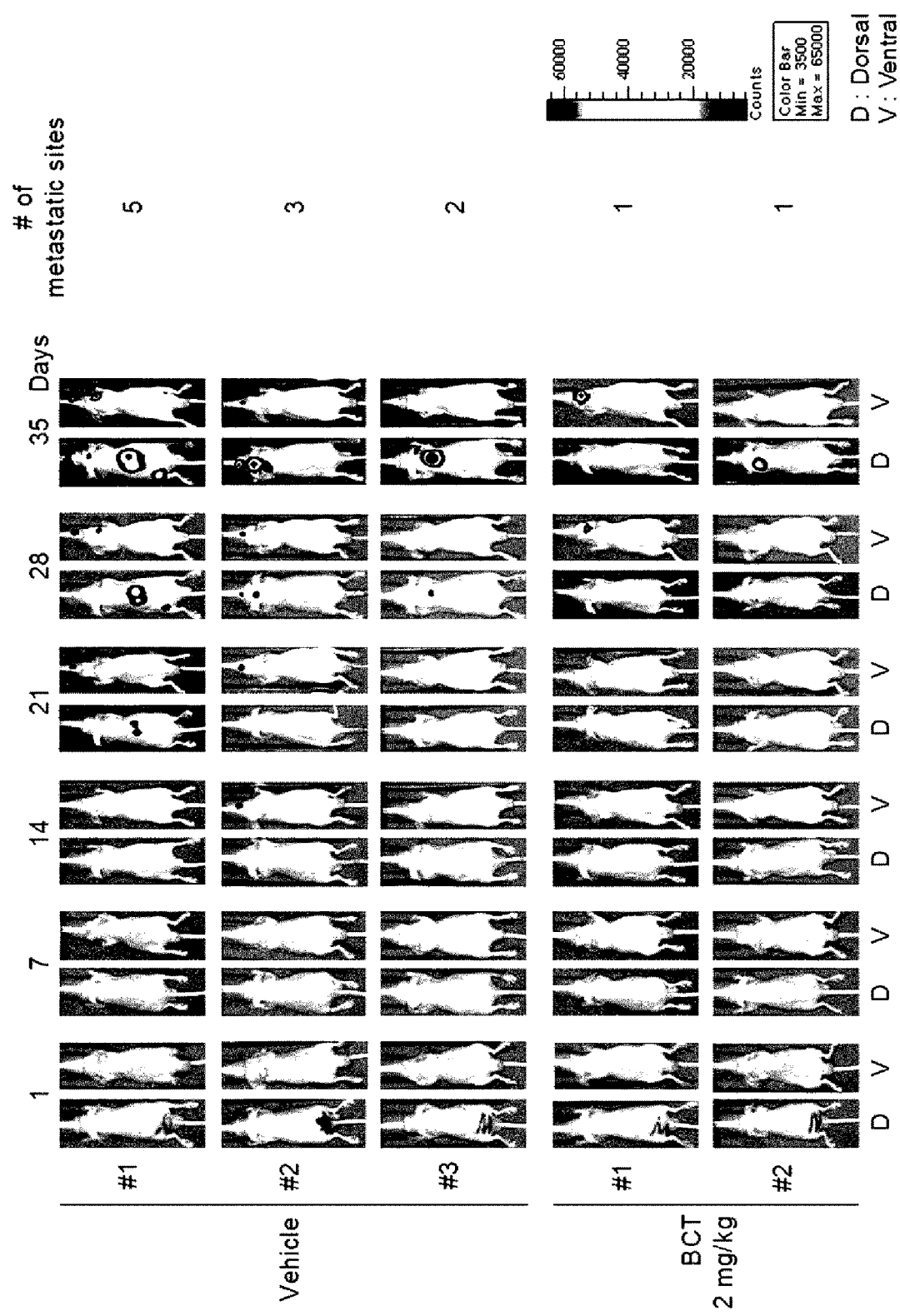
FIG. 14a shows images elucidating inhibitory effects of orally administered bruceantin on metastasis in CRPC xenograft metastasis mouse models according to an embodiment of the present disclosure.
Figure 14B:
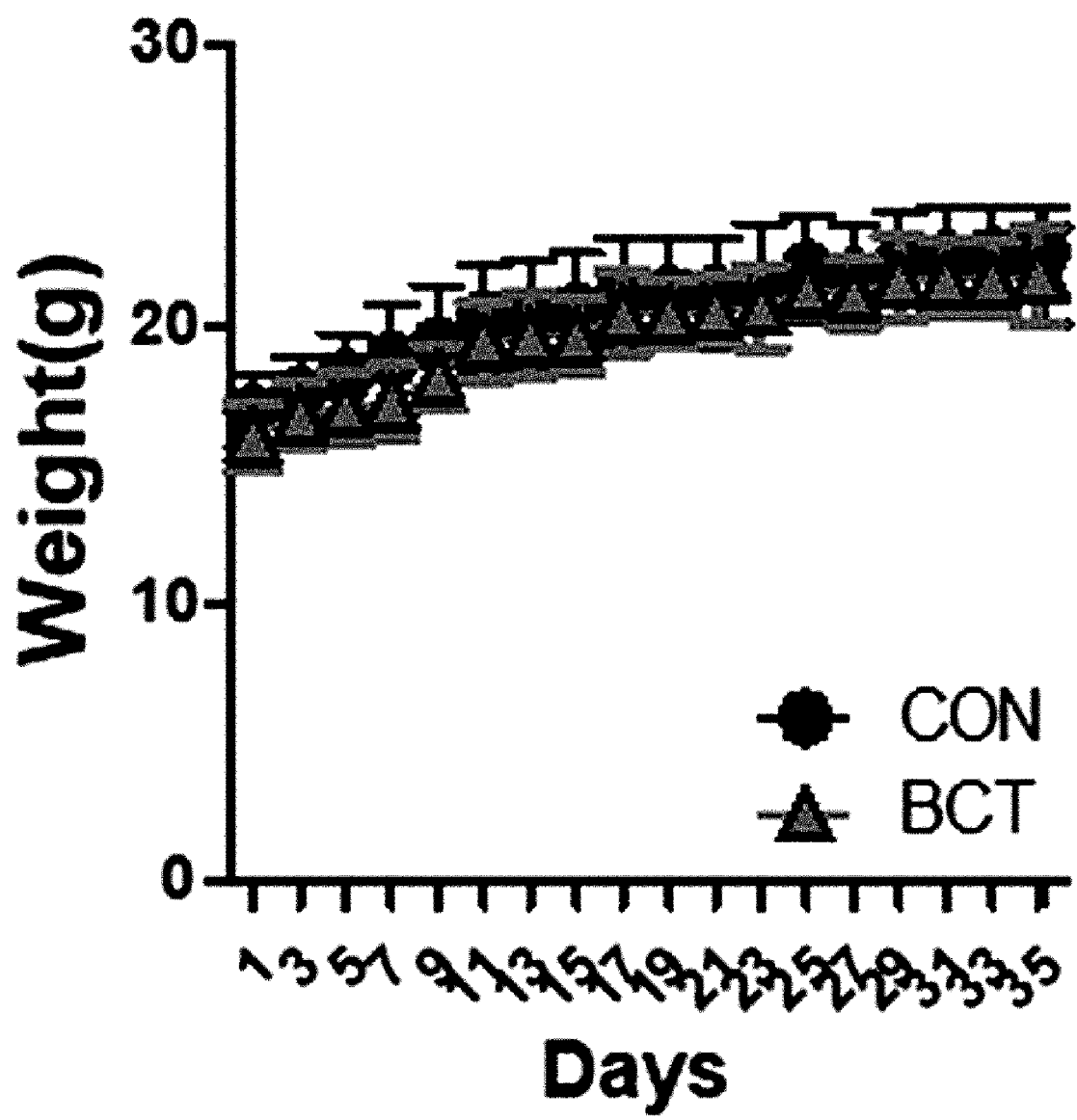
FIG. 14b is a graph showing body weight changes with orally administered bruceantin observed in CRPC xenograft metastasis mouse models accordance to an embodiment of the present disclosure.

As can be seen in FIGS. 14a and 14b and Table 14, bruceantin was found to inhibit metastatic tumor growth and the number of metastases without changing the body weight.

What is claimed is:

1. A method for treating a castration-resistant prostate cancer, the method comprising:
a step of administering to the subject a pharmaceutical composition comprising at least one quassinoid selected from the group consisting of bruceine A, brusatol, and bruceantin.

2. The method of claim 1, wherein the quassinoid is bruceantin.

3. The method of claim 1, wherein the composition is in a formulation form of a pulvis, a granule, a tablet, a capsule, an ointment, a suspension, a syrup, an aerosol, a transdermal agent, a suppository, or a sterile injection.

4. The method of claim 1, wherein the composition is in a formulation form for subcutaneous injection or oral administration.

* * * * *